(12) United States Patent
Stroock et al.

(10) Patent No.: US 8,663,625 B2
(45) Date of Patent: Mar. 4, 2014

(54) DIFFUSIVELY PERMEABLE MONOLITHIC BIOMATERIAL WITH EMBEDDED MICROFLUIDIC CHANNELS

(75) Inventors: Abraham D. Stroock, Ithaca, NY (US); Mario Cabodi, Ithaca, NY (US); Lawrence Bonassar, Ithaca, NY (US)

(73) Assignee: Cornell Research Foundation, Ithaca, NY (US)

(*) Notice: Subject to any disclaimer, the term of this patent is extended or adjusted under 35 U.S.C. 154(b) by 1162 days.

(21) Appl. No.: 11/251,707

(22) Filed: Oct. 17, 2005

(65) Prior Publication Data

US 2006/0173394 A1   Aug. 3, 2006

Related U.S. Application Data

(60) Provisional application No. 60/619,091, filed on Oct. 15, 2004.

(51) Int. Cl.
*A61K 9/00* (2006.01)

(52) U.S. Cl.
USPC ............. 424/93.7; 424/400; 424/422

(58) Field of Classification Search
USPC ............. 424/400, 422, 3.7; 435/325
See application file for complete search history.

(56) References Cited

U.S. PATENT DOCUMENTS

2003/0108587 A1   6/2003  Orgill
2003/0175824 A1*  9/2003  Pishko et al. ............ 435/7.2
2005/0196702 A1*  9/2005  Bryant et al. ............ 430/311

FOREIGN PATENT DOCUMENTS

WO   WO 02/092783 A2   11/2002

OTHER PUBLICATIONS

Cabodi et al., "A Microfluidic Biomaterial," J. Am. Chem. Soc. 127:13788-13789 (2005).
Takayama et al., "Patterning Cells and Their Environments Using Multiple Laminar Fluid Flows in Capillary Networks," Proc. Nat'l Acad. Sci. USA 96:5545-5548 (1999).
Vacanti et al., "Replacement of an Avulsed Phalanx with Tissue-Engineered Bone," N. Engl. J. Med. 344(20):1511-1514 (2001).
Kang et al., "Preparation and Characterization of New Immunoprotecting Membrane Coated with Amphiphilic Multiblock Copolymer," Macromolecular Res 10(2):67-74 (2002).
Dembczynski et al., "Determination of Pore Diameter and Molecular Weight Cut-off of Hydrogel-Membrane Liquid Core Capsules for Immunoisolation," J. Biomaterials Sci 12(9):1051-1058 (2001).
Cabodi et al., "Microfluidics for Vascular Biomaterials," Presentation, Cornell Nanobiotechnology Center (Jun. 7, 2004).
Cabodi et al., "Microvascular Dressing for Burn Applications," Poster Presentation, 14th Annual Meeting and Exhibition of the Wound Healing Society (May 25, 2004).
Cabodi et al., "Microvascular Dressing for Burn Applications," Wound Repair and Regeneration, Abstract 122, 12(2):A32-A32 (published online Apr. 15, 2004).
Gehrke et al., "Factors Determining Hydrogel Permeability," Annals New York Acad. Sci. 831:179-207 (1997).

* cited by examiner

*Primary Examiner* — Ruth Davis
(74) *Attorney, Agent, or Firm* — LeClairRyan, a Professional Corporation

(57) ABSTRACT

The present invention relates to a monolithic biomaterial. The monolithic biomaterial has a primary network of convective flow, microfluidic channels that are embedded in a substrate, where the substrate is diffusively permeable to aqueous solutes. The present invention also relates to a method of making the monolithic biomaterial, as well as methods of using the monolithic biomaterial to facilitate healing of a cutaneous wound of a mammalian subject and of regulating cells.

20 Claims, 15 Drawing Sheets

DIFFUSIVELY PERMEABLE MONOLITHIC BIOMATERIAL WITH EMBEDDED MICROFLUIDIC CHANNELS

This application claims priority benefit of U.S. Provisional Patent Application Ser. No. 60/619,091, filed Oct. 15, 2004, which is hereby incorporated by reference in its entirety.

This invention was made with government support under grant number N00014-04-1-0652, awarded by the Office of Naval Research, and grant numbers ECS-9876771, ECS 03-35765, and DMR 0520404, awarded by the National Science Foundation. The U.S. Government has certain rights in this invention.

FIELD OF THE INVENTION

The present invention relates to a diffusively permeable monolithic biomaterial with embedded microfluidic channels, a method of making the monolithic biomaterial, and methods of using the monolithic biomaterial to facilitate healing of a cutaneous wound of a mammalian subject and to regulate cells.

BACKGROUND OF THE INVENTION

Over one million surgical procedures in the United States each year involve bone and cartilage replacement (Langer et al., *Science* 920:260-266 (1993)). The poor healing characteristics of cartilage have driven the demand for options to replace or supplement damaged tissue. Synthetic materials have been employed for this purpose, but issues of biocompatibility and eventual material failure by fatigue or wear ultimately limit their use. Allografts present an alternative, but their use can be limited by immunological complications, transmission of infectious diseases from the donor, premature resorption of the transplant, and lack of the availability of donor material. As a result, the use of autologous cartilage and/or bone grafts is considered a primary option (Lovice et al., *Otolaryngol. Clin. N. Am.* 32:113-139 (1999)). This approach is hindered by the clinical difficulties associated with harvesting donor tissue. Tissue engineering has been proposed as an alternative route by which tissues are regenerated by cells that are seeded into biodegradable polymer scaffolds that present an appropriate chemical and physical environment for the tissue growth either in vitro or in vivo after re-implantation.

Each year, millions of people suffer severe acute or chronic cutaneous wounds. While great progress has been made in both the fundamental understanding of the biology of wound healing and the clinical treatment of wounds, there are large margins for improvement: acute wounds still require many weeks of treatment, and chronic wounds associated with old age and diabetes still often persist indefinitely. In both the study and treatment of wounds, scientists and doctors lack tools with which to manipulate the wound environment with high spatial and temporal precision. In order to fully control the wound healing process, one must be able to deliver and extract reagents with micrometer-scale spatial resolution (the scale of individual cells) over the macroscopic dimensions of a typical wound, and with minute to hour-scale temporal resolution over the days to weeks of healing.

Tissue engineering holds promise as an approach to generate replacement tissues and organs for those lost by injury or disease. Particular progress has been made in musculoskeletal tissues such as cartilage (Brittberg, M., *Clinical Orthopaedics and Related Research* 367 Suppl.:S147-155 (1999)) and bone (Vacanti et al., *New Eng. J. Med.* 344:1511-1514 (2001)); for these systems, limited clinical success has been achieved. Nonetheless, engineering tissue has been hindered by the lack of sophisticated tools for tailoring the physical and chemical environment of the tissue-forming cells. Recent work has demonstrated success in growing cartilage in 3D scaffolds with physiologically appropriate size and shape; this process is based on injection molding of chondrocyte-seeded gels (Chang et al., *J. Biomed. Mat. Res.* 55:503-511 (2001); Chang et al., *Plastic and Reconstructive Surgery* 112: 793-799 (2003)). Recent advances have also been made in the field of microfluidics, allowing for the control of fluids on micrometer-scales within organic materials (Stone et al., *Annual Review of Fluid Mechanics* 36:381-411 (2004); McDonald et al., *Anal. Chem.* 74:1537-1545 (2002)).

The goal of tissue engineering is to initiate and direct the growth of living tissue for applications which include: studying of basic biological questions, in vitro testing of drugs and environmental agents, and, ultimately, replacing the form and function of compromised tissue in the body by surgical transplantation. Enormous progress has been made over the past few decades toward this goal, with some engineered tissues having entered the clinic (Langer et al., *Principles of Tissue Engineering*, ed., Academic Press: San Diego (2000). A central aspect of successful strategies in tissue engineering is the preparation of an appropriate chemical and mechanical environment in which to grow the tissue cells. Ideally, this environment should be able to mimic aspects of the native environment in which the tissue of interest would have developed in vivo. To this end, important work has been done to tailor the chemical character of the matrix in which tissue cells are embedded (Rowley et al., *Biomat.* 20(1):45-53 (1999)), to assess the effects of physical stimuli (e.g., mechanical and electrical) (Bonassar et al., *J. Ortho. Res.* 19(1):11-17 (2001)), and to assess the effects of soluble chemical stimuli such as growth factors in the media surrounding the growing tissue (Sweigart et al., *Tissue Eng.* 7(2):111-129 (2001)).

In attempting to tailor the environment of a developing tissue, serious consideration must be made of mass transfer to and from each cell in the system. The chemical input and output of a cell is crucial for its basic metabolic functions, and for its interactions with the outside and its neighboring cells. From an engineering stand point, the transfer of soluble species to and from cells in the tissue is one of the principal ways in which information can be delivered and extracted from the tissue, in order to influence and monitor its development. While questions of mass transfer are often discussed in tissue engineering context, there is a lack both of tools with which to implement controlled mass transfer in a growing tissue, and of basic design rules for such a control system.

The creation of a synthetic scaffold that provides the appropriate structural and chemical environment to developing cells is a core strength and challenge of the tissue engineering approach. A variety of synthetic and naturally occurring polymer scaffolds have been used to define both the macroscopic shape and chemistry of the solid structure in which cells can bind (Frenkel et al., *Ann. Biomed. Eng.* 32:26-34 (2004)). Many materials require that cells be seeded into a preformed structure. This post-seeding method has a distinct disadvantage in that the seeding density is typically inhomogeneous, at least initially (Obradovic et al., *Aiche Journal* 46:1860-1871 (2000)). An alternative approach has been introduced based on polymers such as alginate (Chang et al., *J. Biomed. Mat. Res.* 55:503-511 (2001) and agarose (Hung et al., *J. Biomech.* 36:1853-1864 (2003)) that can be solidified under physiological conditions; this method permits the cells to be uniformly suspended in the polymer prior to gelation, leading to a highly homogeneous initial distribution of cells within the scaffold. The form of the polymer-cell gel can be imposed by casting or molding (Chang et al., *J. Biomed. Mat. Res.* 55:503-511 (2001); Chang et al., *Plastic and Reconstructive Surgery* 112:793-799 (2003)). The use of alginate for long term culture of chondrocytes in vitro has been documented extensively (Beekman et al., *Exp. Cell Res.* 237:135-141 (1997); Guo et al., *Connect Tissue Res.* 19:277-297 (1989)). In vivo, alginate has been successfully employed as an injectable vehicle for chondrocyte delivery in the treatment of vesicoureteral reflux (Atala et al., *J. Urology* 150:745-747 (1993)).

A common strategy for controlling the chemical environment of a tissue scaffold is to implant it in a living animal such that the animal's body supplies the basic nutrients, and, perhaps appropriate signals to encourage development (Chang et al., *J. Biomed. Mat. Res.* 55:503-511 (2001)). This technique can pose challenges due to immunological rejection, resorption, and inaccessibility for detailed study of tissue development. As an alternative, in vitro bioreactors have been designed to control the physical and chemical environment of the developing scaffold (Martin et al., *Trends in Biotechnology* 22:80-86 (2004)). In the engineering of cartilage, fluid motion (Freed et al., *Journal of Cellular Biochemistry* 51:257-264 (1993)) and mechanical deformation (Bonassar et al., *J. Ortho. Res.* 19:11-17 (2001)) have been explored as functional characteristics of bioreactors. Fluid motion is introduced primarily to assist mass transfer from the culture medium into scaffolds, but hydrodynamic stresses appear to influence the development of tissue as well (Martin et al., *Biorheology* 37:141-147 (2000)). A variety of modes of fluid motion have been explored: spinner flasks, rotating wall vessels (Martin et al., *Trends in Biotechnology* 22:80-86 (2004)), and perfusion reactors (Pazzano et al., *Biotechnology Progress* 16:893-896 (2000)). No technique has yet been presented that allows for fluid motion to be directed along well-defined paths within a material suitable for use as a tissue scaffold.

The development of microtechnology for the control of fluid behavior has been focused over the past decade on developing small-scale chemical systems for analytical and synthetic manipulations (Stone et al., *Annual Review of Fluid Mechanics* 36:381-411 (2004); Whitesides et al., *Phys. Today* 54:42-48 (2001)). Recently, several groups have also developed microfluidic systems for controlling the culture environment of one or few cells grown in monolayers within a microchannel (Takayama et al., *Proc. Nat'l Acad. Sci. U.S.A.* 96:5545-5548 (1999)). A network of microfluidic channels in a silicon wafer also been used as a substrate on which a monolayer of capillary endothelial cells were grown (Borenstein et al., *Biomedical Microdevices* 4:167-175 (2002)). The group of Borenstein has recently demonstrated the fabrication of microchannels in poly($_{DL}$-lactic-co-glycolide) (PLGA) (King et al., *Advanced Materials* 16:2007-2012 (2004)); these microfluidic structures may be appropriate for use as scaffolds for 3D culture of cells. In general, there is an outstanding challenge to apply microfluidic methods to control the chemical environment of cells in a 3D culture.

The present invention is directed to overcoming these and other deficiencies in the art.

SUMMARY OF THE INVENTION

One aspect of the present invention relates to a monolithic biomaterial. The monolithic biomaterial has a primary network of convective flow, microfluidic channels that are embedded in a substrate, where the substrate is diffusively permeable to aqueous solutes.

Another aspect of the present invention relates to a method of making a monolithic biomaterial having a primary network of convective flow, microfluidic channels within a substrate diffusively permeable to aqueous solutes. This method involves forming a primary network of convective flow, microfluidic channels in a substrate diffusively permeable to aqueous solutes, thereby yielding the monolithic biomaterial.

Another aspect of the present invention relates to a method of facilitating healing of a cutaneous wound of a mammalian subject. This method involves providing a monolithic biomaterial of the present invention. The monolithic biomaterial is contacted with a cutaneous wound of the mammalian subject. At least one healing agent is then introduced into the primary network of microfluidic channels under conditions effective to allow for convective transport of the healing agent through the microfludic channels and for diffusive transport of the healing agent into the substrate, thereby facilitating healing of the wound.

Yet a further aspect of the present invention relates to a method of regulating cells. This method involves providing a monolithic biomaterial of the present invention. Fluids are allowed to flow through the microfluidic channels under conditions effective to regulate cells in or proximate to the monolithic biomaterial.

The monolithic biomaterial of the present invention can be used for various applications, including biomedical applications such as tissue engineering, drug delivery, and prosthetic implantation. These applications demand sophisticated management of the interface between living and synthetic materials. These applications also have encouraged the development of materials with biologically appropriate chemical composition, mechanical properties, rates of degradation, and micro- and macro-structure (Rowley et al., *Biomaterials* 20:45-53 (1999); Altman et al., *Biomaterials* 23:4131-4141 (2002); Boontheekul et al., *Biomaterials* 26:2455-2465 (2005); Vozzi et al., *Biomaterials* 24:2533-2540 (2003); Chang et al., *Journal of Biomedical Materials Research* 55:503-511 (2001), which are hereby incorporated by reference in their entirety). While these synthetic biomaterials have allowed for important advances in biomedical engineering (During et al., *Annals of Neurology* 25:351-356 (1989); Niklason et al., *Science* 284:489-493 (1999), which are hereby incorporated by reference in their entirety), they lack a mechanism to modulate the concentration of soluble species (e.g., metabolites, therapeutics, anti-fouling agents) within their bulk. In living tissues, this function is provided by the microvascular system, a network of convective paths that permeate their volume (Labarbera et al., *American Scientist* 70:54-60 (1982); Colton, C. K., *Cell Transplantation* 4:415-436 (1995), which are hereby incorporated by reference in their entirety). The development of microfluidics, e.g., lithographically-defined channels on a $10-10^3$ μm-scale, has created an opportunity to implement this physiological strategy in synthetic biomaterials.

A successful microfluidic biomaterial ("μFBM")-biomaterial with an embedded microfluidic network—must satisfy the conventional constraints on biomaterials as well as specific constraints for the implementation of microfluidic mass transfer. These constraints are that the material be: (i) appropriate for the replication of microstructure; (ii) formable into pressure-tight fluidic structures; and (iii) highly permeable to the diffusion of small and large solutes. The second constraint requires that the material have an intrinsically low permeability to pressure-driven flow, and that it form a seal with itself and other another materials (e.g., external tubing). The third characteristic is crucial as it allows for diffusive exchange of solute between the microfluidic flows and the bulk of the material. The monolithic biomaterial of the present invention is useful as a microfluidic biomaterial having these characteristics.

The monolithic biomaterial of the present invention is useful for tissue engineering, as the entire process is compatible with pre-seeding of cells within the bulk of the gel (Chang et al., *Journal of Biomedical Materials Research* 55:503-511 (2001), which is hereby incorporated by reference in its entirety). The monolithic biomaterial of the present invention can be used to provide cell-seeded microfluidic biomaterials for creating physiologically accurate environments for the study and control of the development of tissues in vitro. More generally, the monolithic biomaterial of the present invention can be useful for the control of mass transfer in chemical contexts such as reactions mediated by immobilized catalysts or syntheses of materials in gel templates (see Gundiah et al., *Journal of Materials Chemistry* 13:2118-2122 (2003); Guisan et al., *Biotechnology and Bioengineering* 38:1144-1152 (1991), which are hereby incorporated by reference in their entirety).

BRIEF DESCRIPTION OF THE DRAWINGS

FIGS. 7A-7C illustrate the microfabrication of a master structure of microfluidic features in a silicone elastomer. FIG. 7D illustrates the assembly of micro-mold and macro-mold, and injection molding of cell-seeded substrate (e.g., alginate/chondrocyte gel). FIG. 7E illustrates a sealed scaffold with three layers of substrate (e.g., alginate/chondrocyte gel) and two layers of microfluidic structure (i.e., a primary and secondary network of microfluidic channels).

FIG. 8A illustrates the definition of micro-molds (top) and macro-molds (bottom). FIG. 8B illustrates injection molding of the scaffold. FIG. 8C illustrates the release step. FIG. 8D illustrates the assembled scaffold with fluidic connections. FIG. 8E is an magnified view of the fluidic connection.

FIG. 9A is a top view of the monolithic biomaterial, showing inlet portion 171 (synonymous to inlet portion 175 in FIG. 9B) and outlet portion 173 (synonymous to outlet portion 179 in FIG. 9B). FIG. 9B is a cross-sectional view of the monolithic biomaterial, showing primary network of microfluidic channels 31, 33, and 35 embedded in substrate 165 and secondary network microfluidic channels 21, 23, and 25 embedded in substrate 163. FIG. 9B shows that in one embodiment, the microfluidic channels of the networks can be of varying cross-sectional dimensions. FIG. 9C is a detailed cross-sectional view of the monolithic biomaterial and the convective transport of fluid (e.g., healing agent) and diffusive permeation of aqueous solute. Solid vertical arrows show fluid leaking convectively from microfluidic channel 31 to microfluidic channel 21. Squiggly arrows represents diffusive exchange of molecules between fluid contained in microfluidic channel 31 and biocompatible material 220 and through to wound tissue 210. Solid, horizontal arrows show the direction of convective flow of fluids through microfluidic channels 21 and 31. FIG. 9D is a detailed cross-sectional view of the monolithic biomaterial seated in a full-thickness wound bed. Staples 250 can be used to secure the monolithic biomaterial to wound 212. Also depicted are dermis tissue (244), and epidermis tissue (240, 242).

FIG. 10A illustrates half-circuit network having main microfluidic channel 260 with subsidiary microfluidic channels 262, 264, and 266 branching from it. FIG. 10B illustrates a full-circuit network having main microfluidic channels 260 and 261 with subsidiary microfluidic channels 262, 264, and 269 branching from the main microfluidic channels. FIG. 10C illustrates a sequentially branching network having main microfluidic channels 260 with subsidiary microfluidic channels 263, 265, and 267 branching from the main microfluidic channel. FIG. 10D illustrates a reticulate network having main microfluidic channel 171 and subsidiary microfluidic channels 31, 33, and 35.

DETAILED DESCRIPTION OF THE INVENTION

Figure 1:
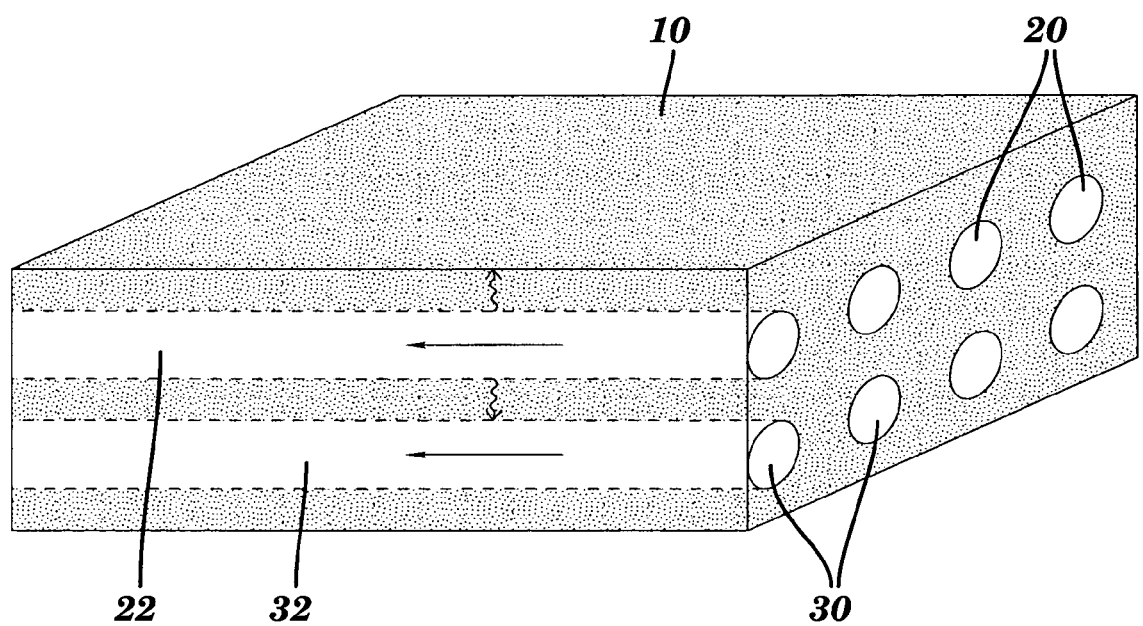
FIG. 1 is a perspective view of an embodiment of the monolithic biomaterial of the present invention.

One aspect of the present invention relates to a monolithic biomaterial. The monolithic biomaterial has a primary network of convective flow, microfluidic channels that are embedded in a substrate, where the substrate is diffusively permeable to aqueous solutes.

As used herein, the term "convective flow, microfluidic channel" refers to a microfluidic channel that is capable of allowing convective flow of fluids through it and that has cross-sectional dimensions of between about $1 \times 10^{-1}$ µm to about $1 \times 10^3$ µm in width and between about $1 \times 10^{-1}$ µm to about $1 \times 10^3$ µm in height.

As used herein, the term "aqueous solutes" refers to materials that can be dissolved and/or suspended in water. Examples of such aqueous solutes can include, without limitation, small molecules, macromolecules, and particulates (e.g., viruses, cells, and cellular material).

As used herein, the term "diffusively permeable to aqueous solutes" is meant to refer to substrates that allow aqueous solutes to move due to gradients in concentration, with or without gradients in pressure.

In one embodiment, the substrate is a hydrogel. Suitable hydrogels can include, without limitation, alginates, acrylate-based hydrogels, collagens, collagen-glycosamino-glycan co-precipitates, agarose, chitosan, fibrin, hyaluronic acid, carrageenan, polyethylene oxide, polypropylene oxide, polyethylene oxide-co-polypropylene oxide, hydroxypropyl methyl cellulose, poly(propylene fumarate-co-ethylene glycol), poly(ethylene glycol)-co-poly(lactic acid), poly(vinyl alcohol), KDL12 oligopeptides, and poly(n-isopropyl acrylamide). A particular hydrogel can include calcium alginate.

In another embodiment, the hydrogel can further include a cross-linking compound. The hydrogels preferably have a controlled rate of crosslinking through the adjustment of environmental variables including, but not limited to, temperature, pH, ionic strength, heat, light, or the addition of chemical crosslinking agents such as calcium, magnesium, barium, chondroitin, sulfate, and thrombin. The cross-linking compound is preferably provided in a weight ratio of hydrogel to cross-linking compound of about 1:100 to 100:1, respectively. In a more preferred embodiment, the weight ratio of cross-linking compound to hydrogel is about 1:5.3. In an even more preferred embodiment, the cross-linking compound is calcium sulfate.

In one embodiment, the substrate can be a hydrogel seeded with a plurality of viable cells. The cells in the hydrogel can be of a single cell type or of multiple cell types. Suitable cell types include, without limitation, all prokaryotic and eukaryotic (e.g., mammalian and plant) cells. Preferred cell types include, without limitation, chondrocytes, osteoblasts, osteoclasts, osteocytes, fibroblasts, hepatocytes, skeletal myoblasts, cardiac myocytes, epithelial cells, endothelial cells, keratinocytes, neurons, Schwann cells, oligodendrocytes, astrocytes, pneumocytes, adipocytes, smooth muscle cells, T cells, B cells, marrow-derived stem cells, hematopeotic stem cells, osteoprogenitor cells, neural stem cells, and embryonic stem cells. The cells can be homogeneously dispersed throughout the hydrogel. Further, the cells can be seeded on or proximate to the walls of the microfluidic channels embedded in the substrate.

The substrate can have various three-dimensional shapes. Suitable three-dimensional shapes can include free-form and anatomic shapes. In a preferred embodiment, the anatomic shape is patient-specific. Suitable anatomic shapes include, without limitation, meniscus and articular shapes.

Figure 9A:
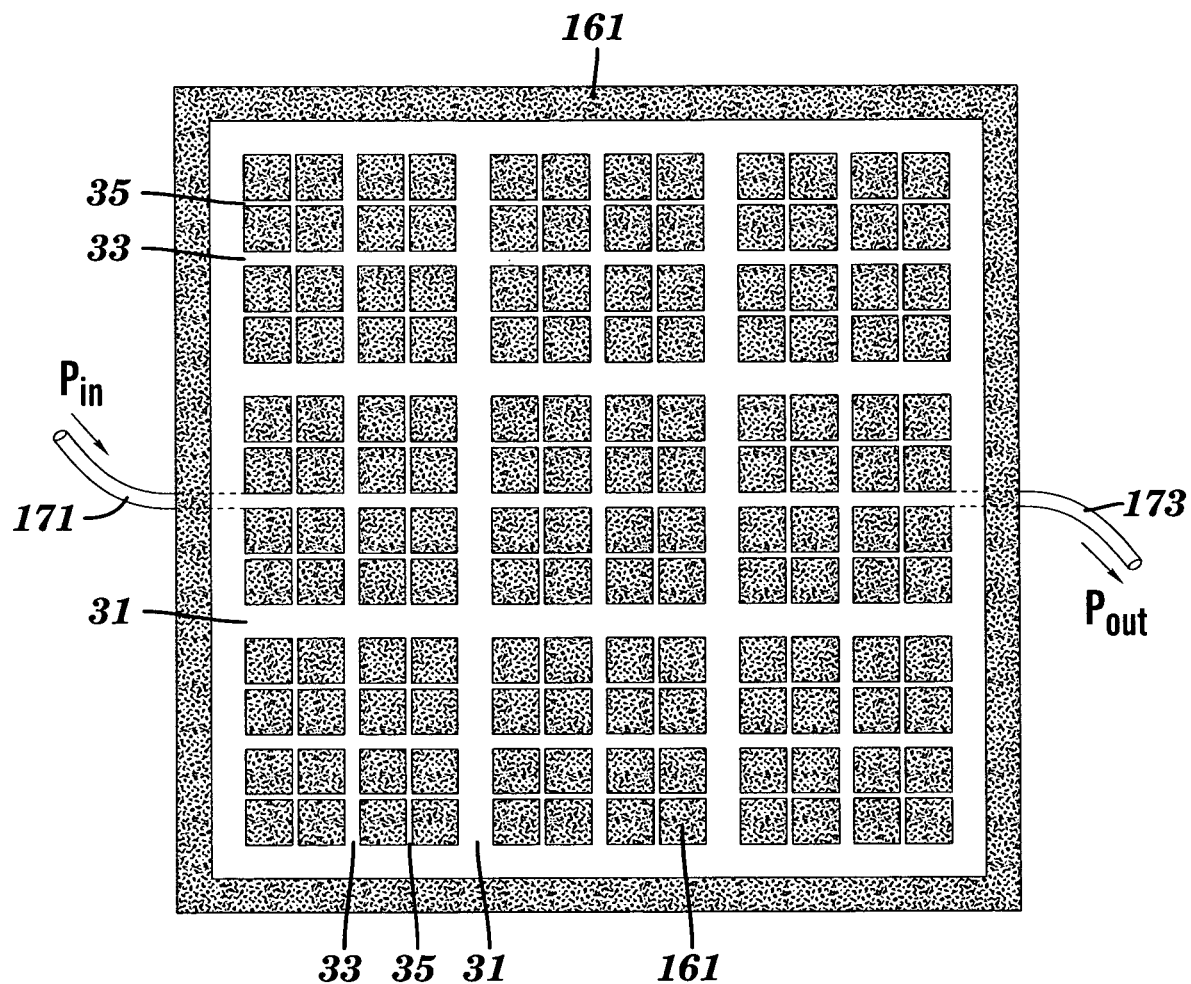
FIGS. 9A-9D show one embodiment of the monolithic biomaterial of the present invention, where the monolithic biomaterial is being used to facilitate healing of a cutaneous wound.
Figure 9B:
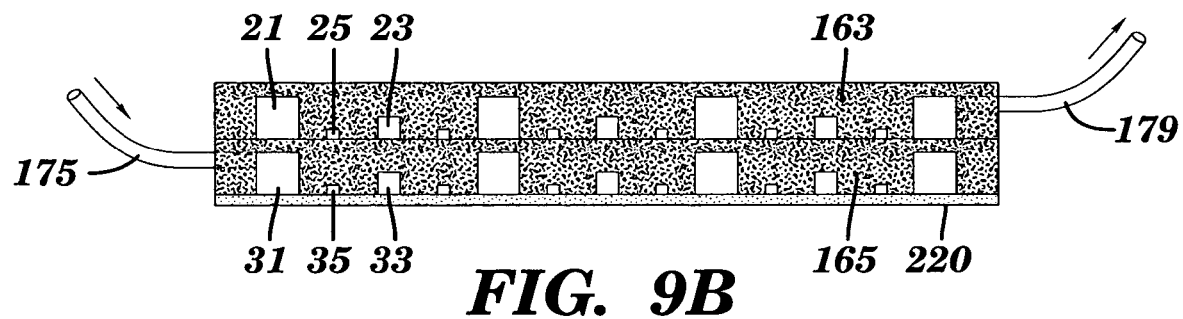
Figure 9C:
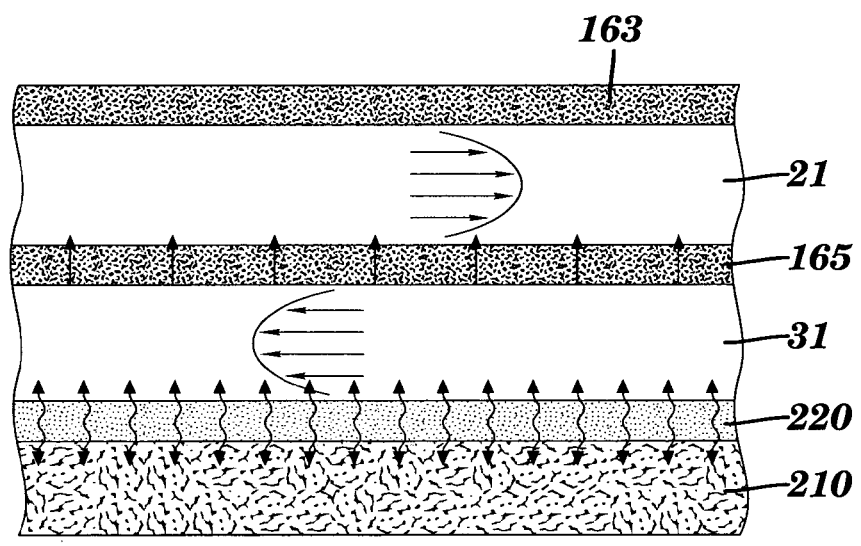
Figure 9D:
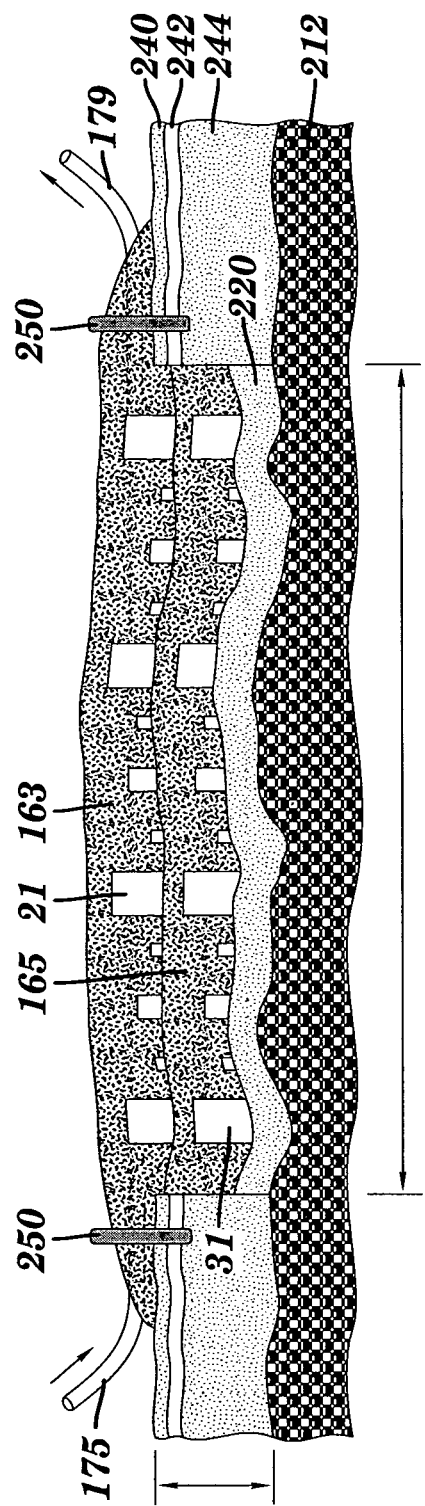
Figure 10A:
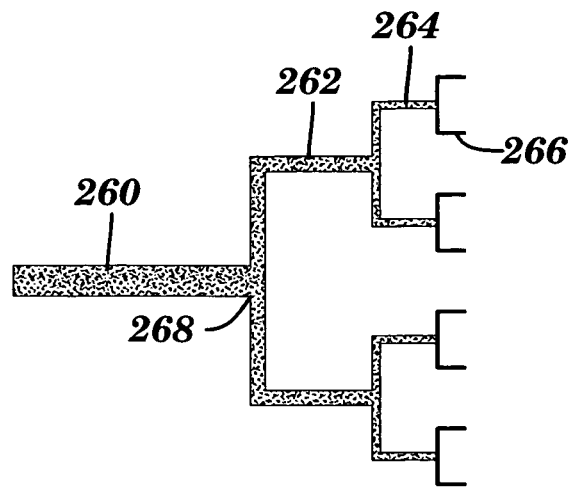
FIGS. 10A-10D are schematic views of various types arrangements of the microfluidic channels of various embodiments of the networks of the monolithic biomaterial of the present invention.
Figure 10B:
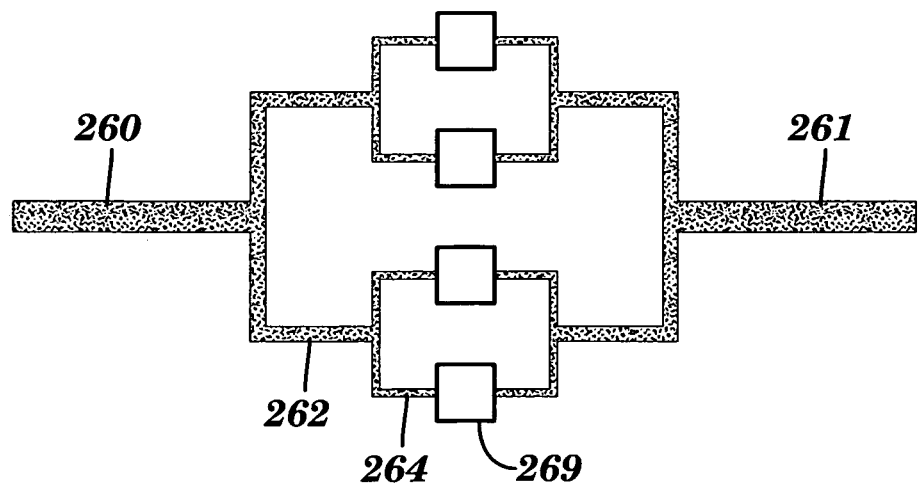
Figure 10C:
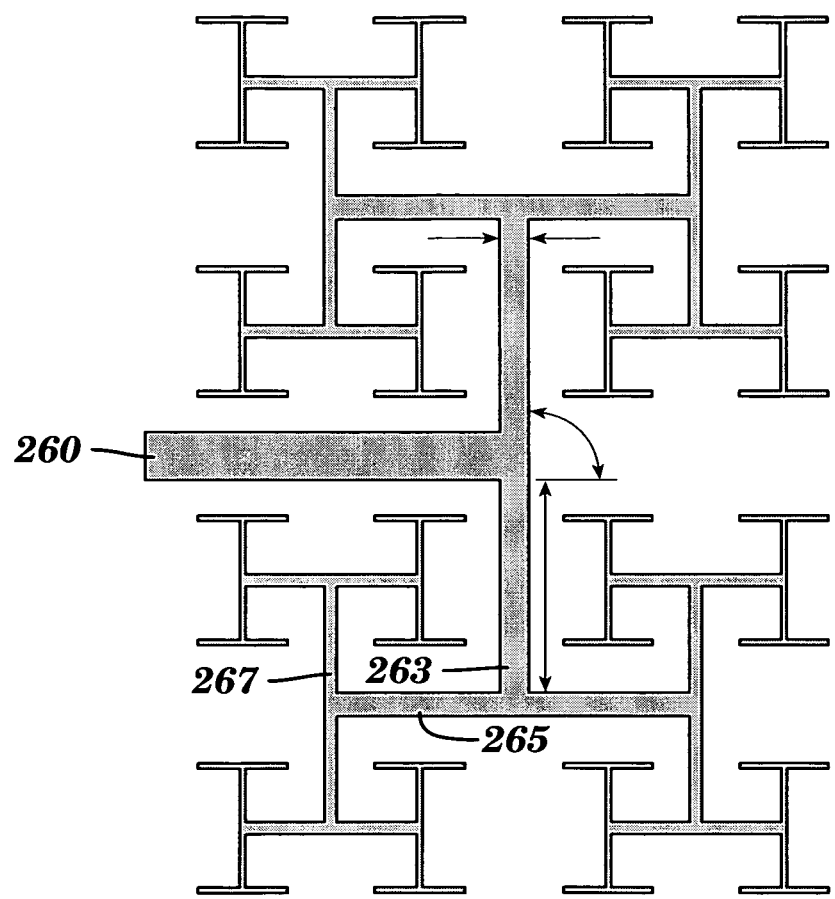
Figure 10D:
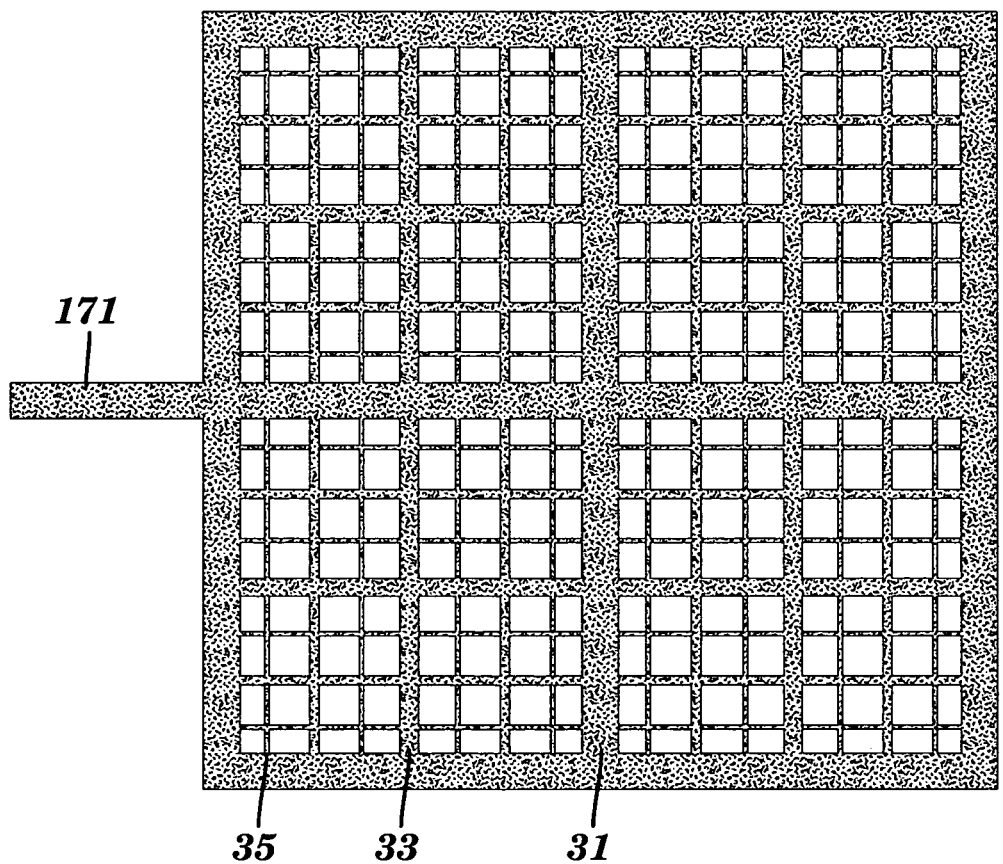

The primary network of microfluidic channels can have various structures. In one embodiment, the primary network of microfluidic channels can include a plurality of main microfluidic channels arranged substantially parallel to one another. In another embodiment, the primary network of microfluidic channels can further include a plurality of subsidiary microfluidic channels arranged substantially perpendicular to the main microfluidic channels. Examples of such an arrangement are illustrated in FIGS. 9A and 10D. In yet another embodiment, the primary network of microfluidic channels can include a plurality of main microfluidic channels having subsidiary microfluidic channels branching from the main microfluidic channels. In a particular arrangement of this type of network, the subsidiary microfluidic channels have cross-sectional dimensions that are smaller than those of the main microfluidic channels. Examples of branching networks are illustrated in FIGS. 10A, 10B, and 10C.

The monolithic biomaterial can also include at least one inlet portion suitable for delivering an incoming fluid into the primary network of microfluidic channels. Examples of such an embodiment are shown in FIGS. 10A, 10C, and 10D. The monolithic biomaterial can further include at least one outlet portion suitable for removing an outgoing fluid from the primary network of microfluidic channels. Examples of such an embodiment are shown in FIGS. 8D and 10B.

In one embodiment, the monolithic biomaterial can include a secondary network of microfluidic channels in the substrate. The secondary network can be independent from the primary network. In another embodiment, the primary network and the secondary network are separated by a diffusively permeable material. Suitable examples of diffusively permeable materials can include, without limitation, a hydrogel (as described herein). In a particular embodiment, the monolithic biomaterial can include at least one inlet portion suitable for delivering an incoming fluid into the primary and secondary network of microfluidic channels and at least one outlet portion suitable for removing an outgoing fluid from the primary and secondary network of microfluidic channels. Examples of such an embodiment are shown in FIGS. 7E, 9A, 9B, and 9D. The secondary network can have varying structures, including, without limitation, those structures described herein above for the primary network. Where the monolithic biomaterial has both a primary and secondary network of microfluidic channels, the structures of the primary and secondary networks can be the same or different.

Another aspect of the present invention relates to a method of making a monolithic biomaterial having a primary network of convective flow, microfluidic channels within a substrate diffusively permeable to aqueous solutes. This method involves forming a primary network of convective flow, microfluidic channels in a substrate diffusively permeable to aqueous solutes, thereby yielding the monolithic biomaterial.

In one embodiment, the primary network is formed by providing a mold having a topography of elevated portions separated by recessed portions. FIG. 3B depicts elevated portion 63 and recessed portion 65 of mold 61. The substrate precursor is then introduced into the mold (see FIG. 4A). Suitable substrate precursors can include, for example, chemical precursors of any of the substrates described herein above. The substrate precursor is then cured under conditions effective to yield a substrate that is diffusively permeable to aqueous solutes and that has a top surface of exposed microfluidic channels separated by channel-defining walls. The top surface of the substrate is then sealed with a sealing component, thereby fully enclosing the microfluidic channels as the primary network of microfluidic channels in the substrate.

In one embodiment, the mold is prepared using photolithography. Photolithographic techniques for use in this invention are described in more detail below.

The sealing component can be prepared by molding.

In another embodiment, this method further includes attaching at least one inlet portion and at least one outlet portion to the primary network of microfluidic channels, where the inlet portion is suitable for delivering an incoming fluid into the primary network of microfluidic channels and the outlet portion is suitable for removing an outgoing fluid from the primary network of microfluidic channels.

FIG. 1 illustrates a monolithic biomaterial having a primary and secondary network of microfluidic channels. Microfluidic channels 20 and 30 are embedded in substrate 10, which is diffusively permeable to aqueous solutes. Microfluidic channels 20 are part of the primary network and microfluidic channels 30 are part of the secondary network. Microfluidic channels 22 and 32 are cutaway views of microfluidic channels 20 and 30, respectively. These cutaway views illustrate the convective flow (solid, horizontal arrows) of material (e.g., fluid) through the microfluidic channels and the diffusive permeation (squiggly arrows) of material from the microfluidic channels.

FIGS. 2-6 illustrate one embodiment of the method of making a monolithic biomaterial of the present invention. The monolithic biomaterial embodiment shown in FIGS. 2-6 has just one network of microfluidic channels (e.g., a primary network).

Figure 2A:
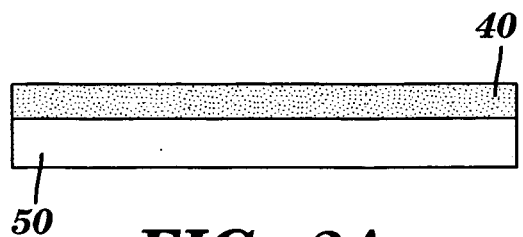
FIGS. 2A-2B are cross-sectional views of one embodiment of the photolithography step involved in making the monolithic biomaterial of the present invention, where the biomaterial has a primary network of microfluidic channels.
Figure 2B:
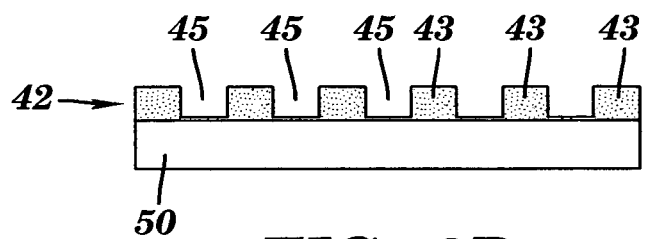
Figure 3A:
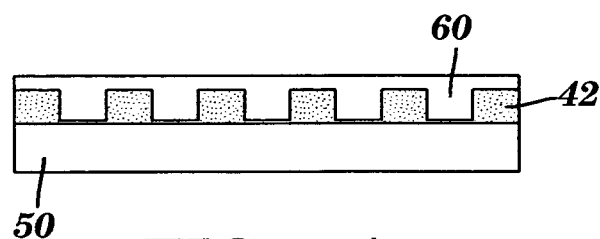
FIGS. 3A-3B are cross-sectional views of one embodiment of the elastomer molding and release step involved in making the monolithic biomaterial of the present invention, where the biomaterial has a primary network of microfluidic channels.
Figure 3B:
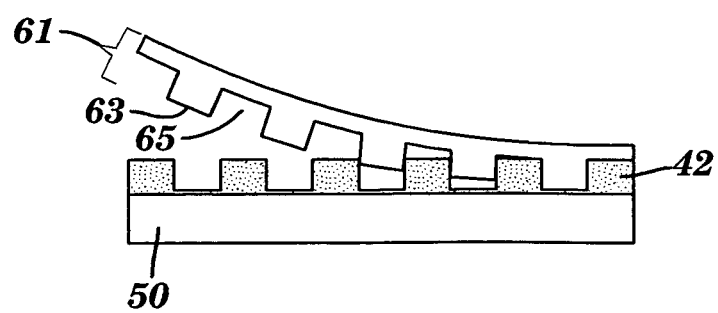

FIGS. 2A, 2B, 3A, and 3B illustrate preparation of a microfluidic channel network mold master using photolithography. As shown in FIG. 2A, photoresist 40 (e.g., SU-8) is deposited on wafer 50 (e.g., 4-inch silicon wafer) to create first master mold 42. FIG. 2B shows first master mold 42 having elevated portions 43 and recessed portions 45 after subjecting photoresist 40 to photolithography. As shown in FIG. 3A, pre-polymer 60 (e.g., poly(dimethylsiloxane) ("PDMS")) is poured into first master mold 42 and allowed to cure. One method for curing pre-polymer 60 is in an oven at 60° C. for 2 hours. As illustrated in FIG. 3B, after curing, second master mold 61 can be released for further use in preparing the monolithic vascular round two of the present invention. Second master mold 61 is shown to have elevated portions 63 and recessed portions 65.

Figure 4A:
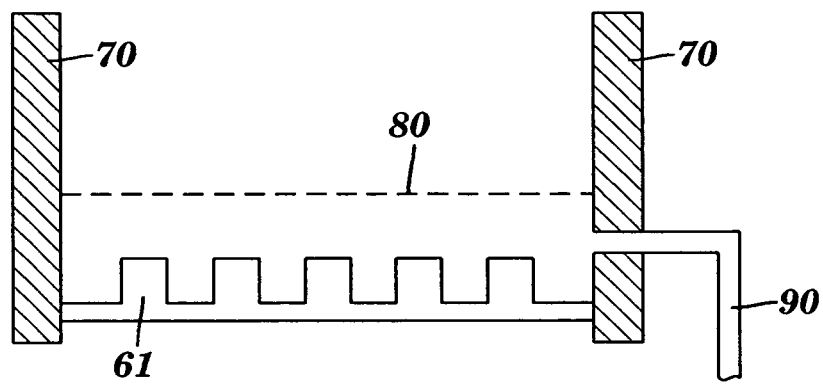
FIGS. 4A-4B are cross-sectional views of one embodiment of the mold assembly step involved in making the monolithic biomaterial of the present invention, where the biomaterial has a primary network of microfluidic channels.
Figure 4B:
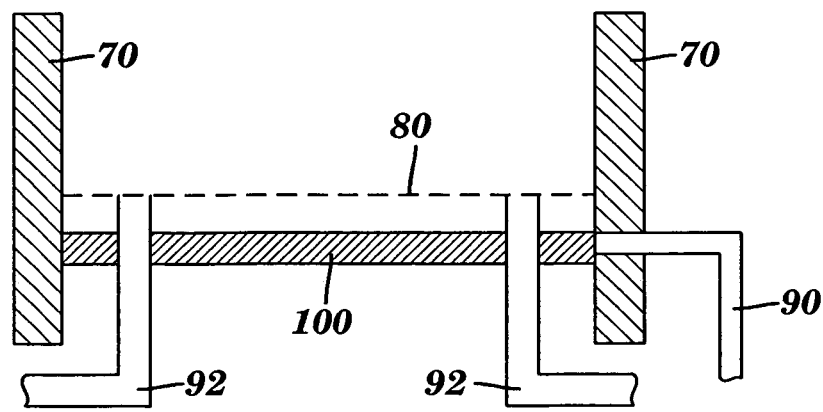

FIGS. 4A and 4B illustrate mold assembly, where FIG. 4A depicts a jig for a top layer of substrate (i.e., a micro-structured layer) and FIG. 4B depicts a jig for a bottom layer of substrate (i.e., an unstructured layer). Both jigs are sealed with membrane 80 (e.g., a track-etch polycarbonate membrane). Supports 70 provide support and side boundaries for molding. In FIG. 4B, glass slide 100 with pre-set tubing 92 can be used to provide support for assembling the substrate structure and for facilitating fluidic connections between the embedded micrfluidic channels of the networks.

Figure 5A:
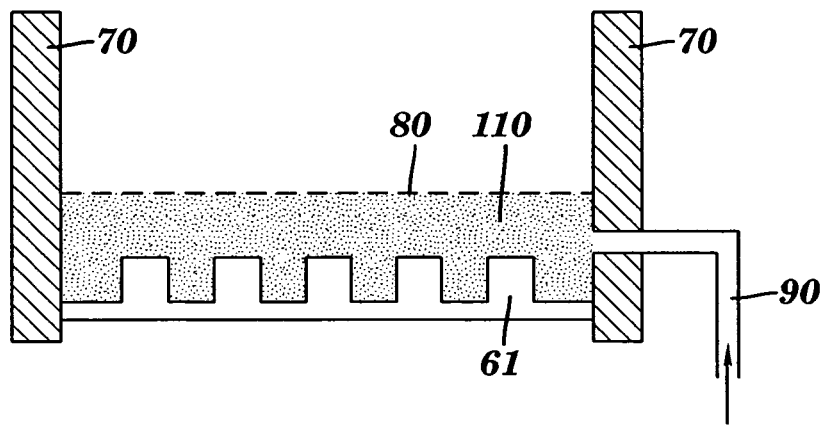
FIGS. 5A-5B are cross-sectional views of one embodiment of the hydrogel injection (FIG. 5A) and hydrogel curing (FIG. 5B) steps involved in making the monolithic biomaterial of the present invention, where the biomaterial has a primary network of microfluidic channels.
Figure 5B:
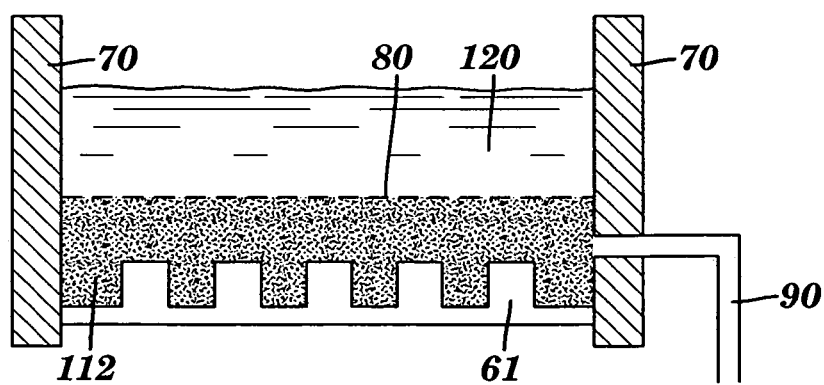

FIGS. 5A and 5B illustrate the process of substrate precursor injection (e.g., hydrogel injection) (FIG. 5A) and curing of the substrate precursor (FIG. 5B). For example, FIG. 5A shows second master mold 61 with substrate precursor 110 (e.g., an uncrosslinked hydrogel) injected into second master mold 61. FIG. 5B shows cross-linking compound 120 (e.g., $CaCl_2$) placed in the upper reservoir of the jig above membrane 80, allowing for substrate precursor 110 (see FIG. 5A) to form into substrate 112. Tubing 90 (shown in FIGS. 4A, 4B, 5A, and 5B) can be used to inject precursor 110.

Figure 6A:
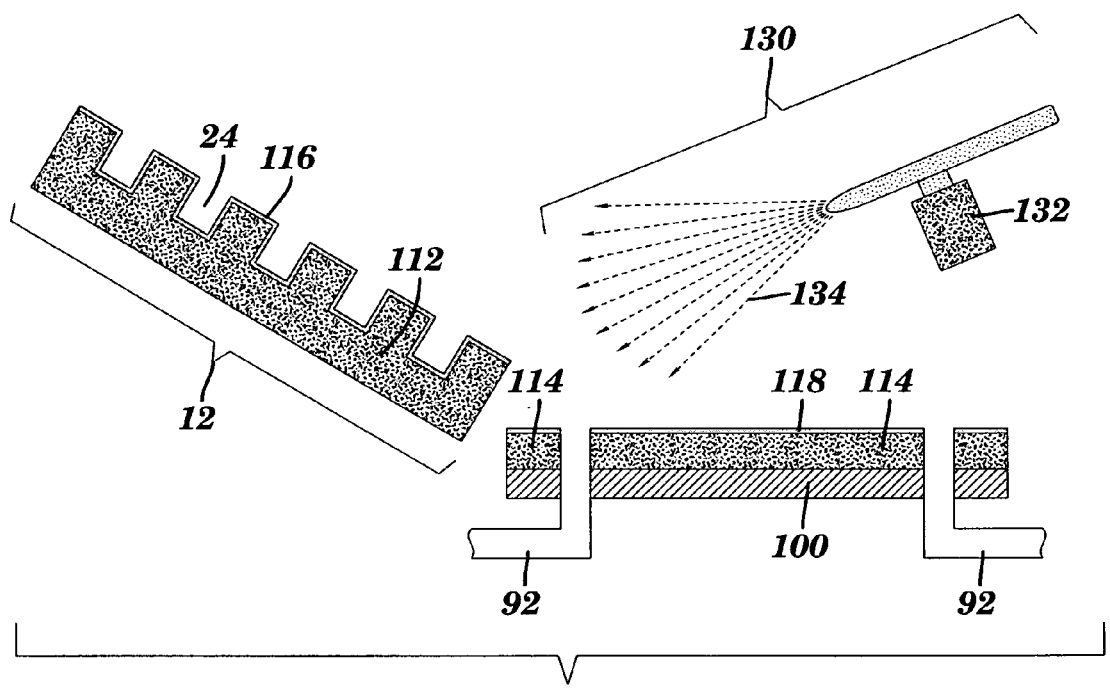
FIGS. 6A-6B are cross-sectional views of one embodiment of the surface melt (FIG. 6A) and sealing (FIG. 6B) steps involved in making the monolithic biomaterial of the present invention, where the biomaterial has a primary network of microfluidic channels.
Figure 6B:
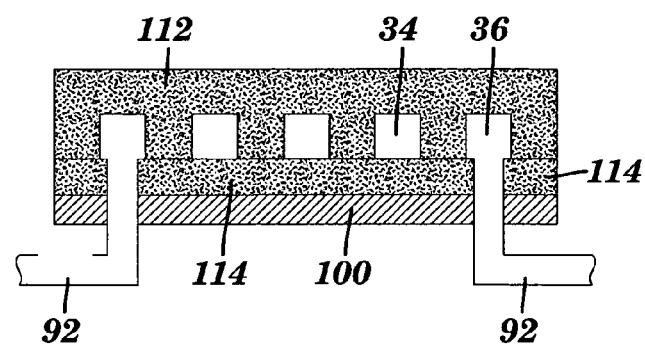

FIGS. 6A and 6B illustrate the surface dissolution (FIG. 6A) and sealing (FIG. 6B) steps of one embodiment of the method of making the monolithic biomaterial (having a primary network of microfluidic channels) of the present invention. Layer 114 represents a bottom layer, while layer 12 represents a top layer, both of which were produced during the molding steps depicted in FIGS. 4A, 4B, 5A, and 5B. As shown in FIG. 6A, surface 116 of substrate 112 (e.g., a calcium alginate hydrogel) and/or surface 118 of substrate 114 (e.g., a calcium alginate hydrogel) can be treated with soluble chelator 132 (e.g., sodium citrate) (depicted as a spray exiting from applicator 132 in view 130), which dissolves a portion of substrate 112 (e.g., dissolves surface 116) and substrate 114 (e.g., dissolves surface 118). Once soluble chelator 132 is applied to surfaces 112 and 114, these surfaces can be placed in contact with one another to allow uncrosslinked chains of the surfaces to interpenetrate. Recessed portions 24 of substrate 112 then form embedded microfluidic channels 34 and 36 (see FIG. 6B). As illustrated in FIG. 6B, a cross-linking compound (e.g., $CaCl_2$) can then be injected into the microfluidic channels (e.g., microfluidic channels 34 and 36) through pre-set tubing 92, allowing dissolved portions of substrates 112 and 114 to re-gel and form a seal.

FIGS. 8A-8E schematically illustrates various aspects of another embodiment of the method of making a monolithic biomaterial of the present invention. Like in FIGS. 2-6, the monolithic biomaterial schematically shown in FIG. 8D also has just one network of microfluidic channels.

Figure 8A:
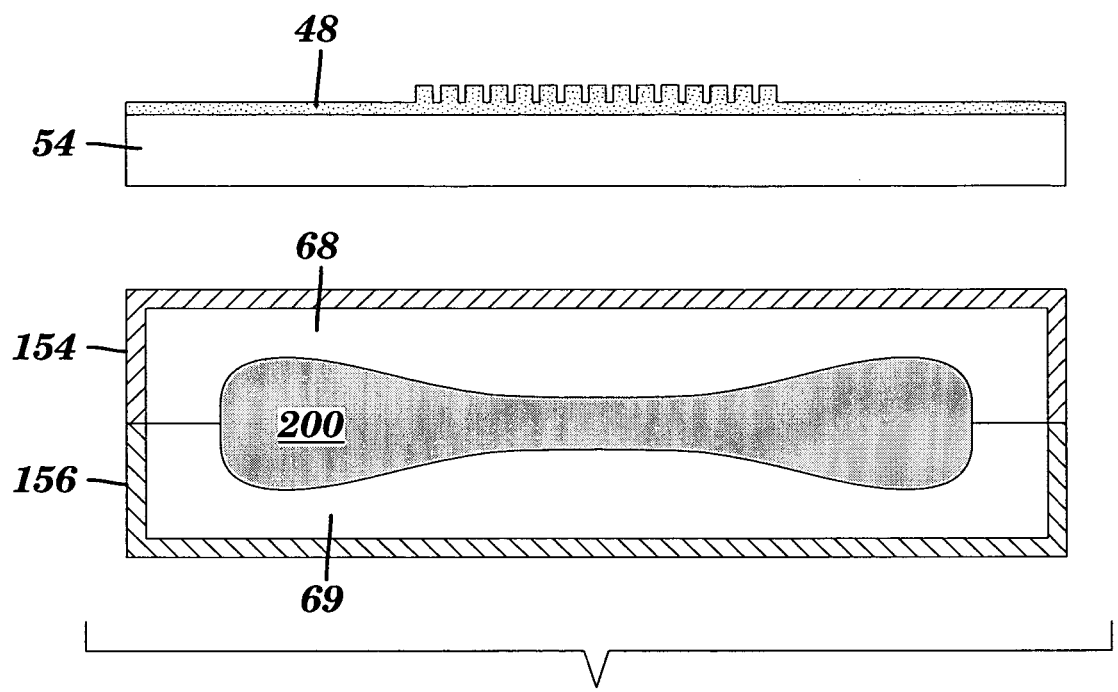
FIGS. 8A-8E are cross-sectional views of one embodiment of the process for fabricating a monolithic biomaterial of the present invention, where the monolithic biomaterial has a primary network of microfluidic channels and inlet and outlet portions.

FIG. 8A shows a micro-mold (top) and two macro-molds (bottom). The micro-mold includes wafer 54 (e.g., a silicon wafer) having master micro-mold 48, which includes a desired pattern of elevated and recessed portions. Master macro-molds 68 and 69 are shown to be encased in mold casings 154 and 156, respectively. Master macro-molds 68 and 69 (as shown in FIG. 8A) can each be used along with master micro-mold 48 to define the shape of the monolithic biomaterial of this embodiment, where master macro-molds 68 and 69 define the macro-structure and master micro-mold 48 defines the micro-structure of the monolithic biomaterial.

Figure 8B:
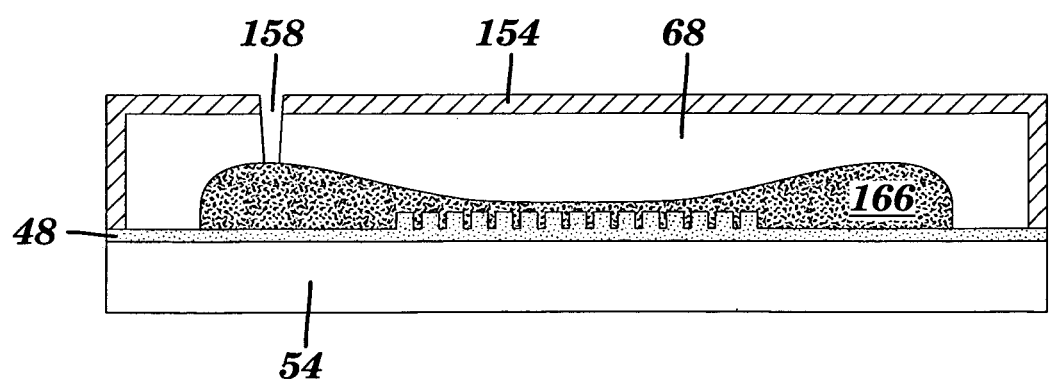

FIG. 8B shows a micro-mold (including wafer 54 and master micro-mold 48) and a macro-mold (including mold casing 154 and master macro-mold 168) combined to allow for injection of substrate precursor 166, which can be injected via opening 158. Substrate precursor 166 is subjected to curing to produce subtrate 168 (see FIG. 8C).

Figure 8C:
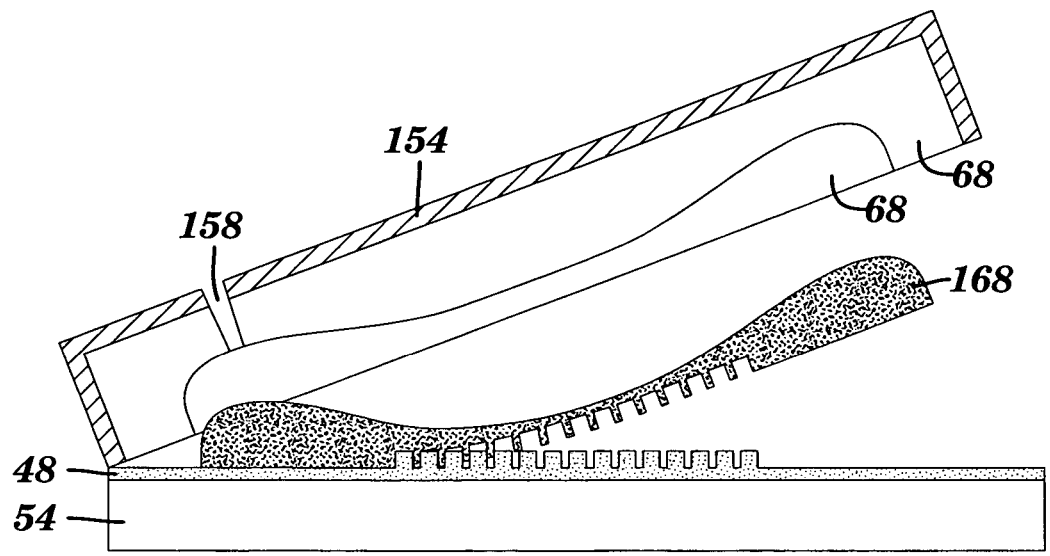
Figure 8D:
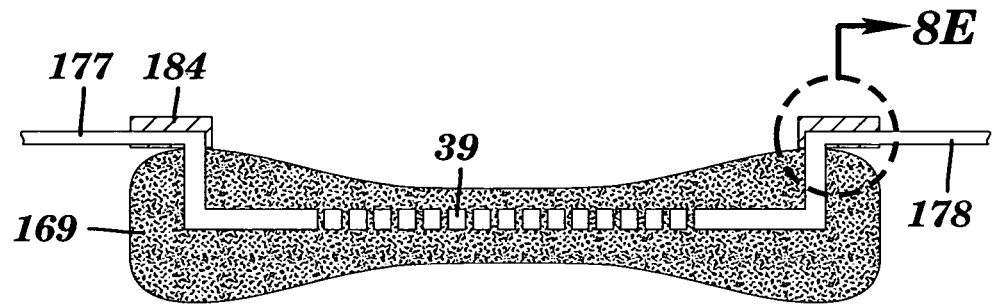

FIG. 8C shows the releasing of substrate 168 from the macro-mold and the micro-mold. The steps depicted in FIGS. 8A-8C can be performed multiple times to produced multiple substrates 166 having micro-structures.

Figure 8E:
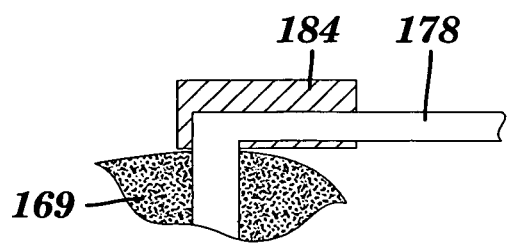

FIG. 8D shows one embodiment of a monolithic biomaterial of the present invention, which can be produced by combining two substrates 166 to form a single substrate 169 having microfluidic channels 39 embedded therein. FIG. 8D also shows inlet portion 177 and outlet portion 178, both of which are connected to the network of microfluidic channels. Connector 184 can be used to connect the network of microfluidic channels (including microfluidic channels 39) to external tubing (e.g., inlet portion 177 and outlet portion 178). FIG. 8E is an isolated view of such a connection.

In yet another embodiment, the method of making the monolithic biomaterial of the present invention can involve making a monolithic biomaterial having more than one network of microfluidic channels. For example, the method can produce a monolithic biomaterial having a primary and secondary network of microfluidic channels (see, e.g., FIGS. 1, 7E and 9D). In such an embodiment, these networks can be formed by providing a mold having a topography of elevated portions separated by recessed portions. A substrate precursor is then introduced into the mold. The substrate precursor is cured under conditions effective to yield a diffusive permeable substrate that is diffusively permeable to aqueous solutes and that has a top surface of exposed microfluidic channels separated by channel-defining walls. The substrate is removed from the mold to produce a first molded material. The introducing, curing, and removing steps described above are then repeated to produce a second molded material. Thereafter, the first and second molded materials are joined to form a secondary network of microfluidic channels in the substrate, where the secondary network is independent from the primary network.

In one embodiment, the method of making the monolithic biomaterial can further include providing a layer of diffusively permeable material between the primary network and the secondary network before joining the first and second molded materials.

In another embodiment, the method of making the monolithic biomaterial can also include attaching at least one inlet portion and at least one outlet portion to the primary and secondary network of microfluidic channels, where the inlet portion is suitable for delivering an incoming fluid into the secondary network of microfluidic channels and the outlet portion is suitable for removing an outgoing fluid from the primary and secondary network of microfluidic channels.

Figure 7A:
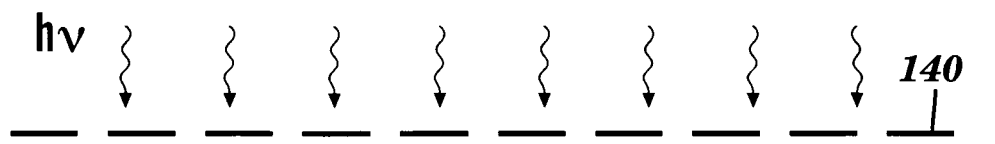
FIGS. 7A-7E are cross-sectional views of one embodiment of method of fabricating a monolithic biomaterial of the present invention, where the biomaterial has a primary and a secondary network of microfluidic channels.
Figure 7B:
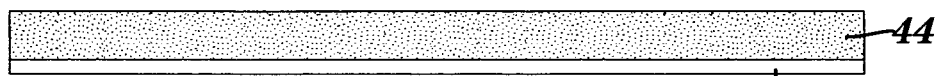
Figure 7C:
Figure 7D:
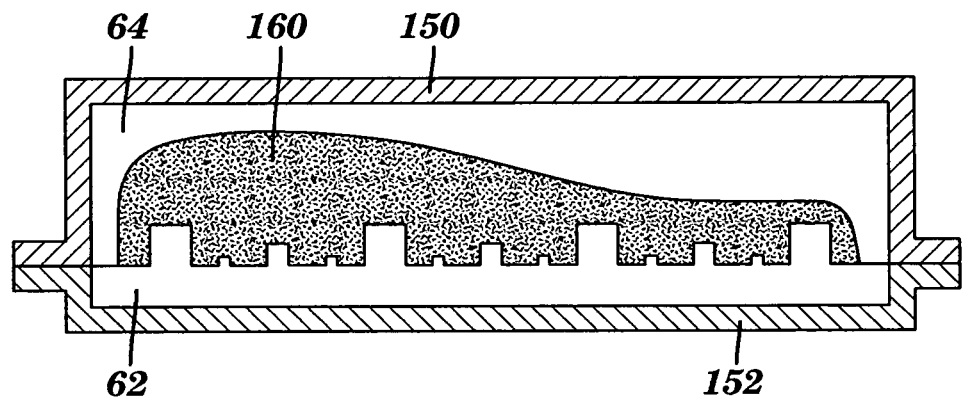
Figure 7E:
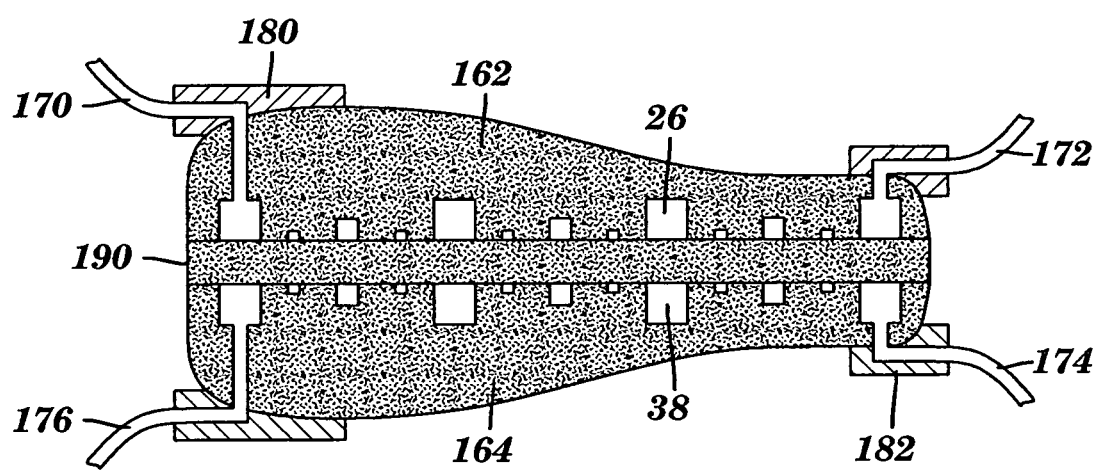

As an example, FIGS. 7A-7E depict one embodiment of the method of making a monolithic biomaterial of the present invention having primary and secondary networks that are independent from one another. FIGS. 7A-7C illustrate the microfabrication of a master structure of microfluidic features in a silicone elastomer. FIG. 7D illustrates the assembly of micro-mold and macro-mold, and injection molding of cell-seeded substrate (e.g., alginate/chondrocyte gel). FIG. 7E illustrates a sealed scaffold with three layers of substrate (e.g., alginate/chondrocyte gel) and two layers of microfluidic structure (i.e., a primary and secondary network of microfluidic channels).

In particular, FIG. 7A shows photoresist 44 (e.g., silicone elastomer) deposited on silicon wafer 52, with photomask 140 above photoresist 44. The vertical, squiggly lines represent suitable electromagnetic radiation (e.g., UV radiation). FIG. 7B depicts treated photoresist 46 having microfluidic features. FIG. 7C shows micro-mold 62 (e.g., silicone) formed pouring a micro-mold precursor in photoresist 46.

FIG. 7D illustrates the assembly of micro-mold 62 and macro-mold 64, and injection molding of substrate precursor 160 (e.g., cell-seeded substrate such as alginate/chondrocyte gel). Macro-mold 64 can be fabricated is discussed herein below. Mold casings 150 and 152 can be used to assemble macro-mold 64 and micro-mold 62, respectively, to allow for injection of substrate precursor 160 into the combined macro/micro-mold. Substrate precursor 160 is then cured in order to yield a substrate for use in the monolithic biomaterial of the present invention. The combined macro/micro-mold can be used to perform multiple injections of substrate precursor 160, thereby yield multiple substrates.

As shown in FIG. 7E, two such substrates (e.g., substrate 162 and substrate 164) can be combined to form two networks of microfluidic channels. FIG. 7E depicts an embodiment of a monolithic biomaterial of the present invention having a primary and secondary network of microfluidic channels. FIG. 7E shows layer 190 (i.e., the diffusively permeable material) between microfluidic channel 26 of a secondary network and microfluidic channel 38 of a primary network. As shown in FIG. 7E, the depicted embodiment of the monolithic biomaterial of the present invention includes three layers of substrate: layer 190; substrate 162; and substrate 164. All three of these layers of substrate can be of the same composition (e.g., alginate-chondrocyte gels). This depicted embodiment shows layer 190 serving yield a structure where microfluidic channel 26 is embedded in substrate 162 (and layer 190), and where microfluidic channel 38 is embedded in substrate 164 (and layer 190). Inlet portion 170 and outlet portion 172 connect to the microfluidic channels of the secondary network, while inlet portion 176 and outlet portion 174 connect to the microfluidic channels of the primary network.

Calcium alginate has been used extensively for tissue engineering (Rowley et al., *Biomaterials* 20:45-53 (1999); Chang et al., *Journal of Biomedical Materials Research* 55:503-511 (2001), which are hereby incorporated by reference in their entirety), cell culture (Seifert et al., *Biotechnology Progress* 13:562-568 (1997), which is hereby incorporated by reference in its entirety), and drug delivery (Gombotz et al., *Advanced Drug Delivery Reviews* 31:267-285 (1998), which is hereby incorporated by reference in its entirety); its attractive intrinsic properties include: low cytotoxicity, biodegradability, ability to be molded under mild conditions, mechanical stability at low solid fractions, and high permeability to diffusive mass transfer (Li et al., *Biotechnology and Bioengineering* 50:365-373 (1996), which is hereby incorporated by reference in its entirety). Thus, in accordance with the methods of the present invention, soft lithography (McDonald et al., *Analytical Chemistry* 74:1537-1545 (2002), which is hereby incorporated by reference in its entirety) can be used to form a sealed microfluidic network in calcium alginate with pressure-tight connections to external tubing. As discussed in more detail below, the key steps in this process are micro-molding of slabs of gel onto lithographically-defined masters, and bonding of distinct slabs of the gel to form a sealed structure. To achieve bonding, the surfaces of the slabs can be dissolved by applying sodium citrate (the citrate removes the calcium cross-links by chelating calcium) (Masuda et al., *Journal of Orthopaedic Research* 21:139-148 (2003), which is hereby incorporated by reference in its entirety), the dissolved surfaces placed in contact with one another, and the melted interfaces re-gelled with the application of calcium chloride.

The adaptation of lithographic techniques of microfabrication for use in silicones has proven to be successful for a variety of applications (Xia et al., *Angew. Chem. Int. Ed. Engl.* 37:550-575 (1998), which is hereby incorporated by reference in its entirety), including microfluidics (Whitesides et al., *Phys. Today* 54:42-48 (2001), which is hereby incorporated by reference in its entirety). These techniques can be adapted for use in acrylate-based hydrogels (poly(acrylamide), poly(hydroxyethyl methacrylate), and poly(ethyleneglycol) diacrylate), as well as in calcium-alginate gels, such as those used as 3-D scaffolds for the culture of chondrocytes. The general methodology includes the following aspects (as discussed in more detail below): (i) photolithographic definition of microchannel networks; (ii) definition of silicone master structure; (iii) alginate gels; (iv) transfer of network geometry into thin slabs of calcium alginate gel; and (v) sealing to form multilayered structures and sealed microfluidic networks.

Photolithographic Definition of Microchannel Networks:

Photolithographic definition of microchannel networks can be performed as follows. The desired pattern of the network is drawn with a computer drawing program (L-Edit) and exported to a Pattern Generator for the creation of a photomask with features of minimum dimension of 2 µm. A negative photoresist (SU-8, MicroChem, Newton, Mass.) is spin cast onto a 4-inch diameter silicon wafer; the thickness (1 µm<t<1 mm) of the layer of photoresist defines the thickness of the final features. Pre-bake, UV-exposure, post-bake, and development are performed in a manner that closely follows the manufacturer's recommendations (www.microchem. com). Multilayer structures are made by repeating the above procedure (spin casting through exposure) with the desired thicknesses and photomasks. The ability to form multi-layered structures is important for defining microfluidic networks with multiple sizes of channels. In order to account for two molding steps in the transfer of this pattern, this lithographic procedure is designed to create a positive image of the desired channel structure (i.e., the features corresponding to channels are grooves in the photoresist).

Definition of Silicone Master Structure:

The surface of the resist-on-wafer structure is passivated with the deposition of a fluorinated silane to avoid adhesion of the silicone (McDonald et al., *Anal. Chem.* 74:1537-1545 (2002), which is hereby incorporated by reference in its entirety). A silicone (Sylgard 184, Dow Corning, Midland, Mich.) impression of the structure is formed.

Alginate Gels:

Acellular solutions of calcium-alginate pre-gels can be those as described for cellular in Chang et al., *J. Biomed. Mat. Res.* 55:503-511 (2001) and Chang et al., *Plastic and Reconstructive Surgery* 112:793-799 (2003), which are hereby incorporated by reference in their entirety.

Transfer of network Geometry into Thin Slabs of Calcium Alginate Gel:

The silicone master is laid on a rigid Plexiglas backing and assembled with a piece of glass in an aluminum jig; a polycarbonate spacer of precisely controlled thickness (down to ~25 μm) defines the thickness of the gap between the silicone and the glass; this thickness defines the maximum thickness of the molded gel. The pre-gel is injected with a syringe into the gap between the silicone master and the glass. Gelled structures are removed from the jig after 10 minutes, and allowed to further cross-link in a buffered solution of $CaCl_2$ (80 mM $CaCl_2$, 49 mM NaCl, 25 mM HEPES) for 1 hour. This curing step in $CaCl_2$ has been employed successfully with chondrocyte-seeded scaffolds (Chang et al., *J. Biomed. Mat. Res.* 55:503-511 (2001); Chang et al., *Plastic and Reconstructive Surgery* 112:793-799 (2003); Stevens et al., *Biomat.* 25:887-894 (2004), which are hereby incorporated by reference in their entirety).

Sealing to Form Multilayered Structures and Sealed Microfluidic Networks:

The reversible nature of the calcium-mediated cross-links in the gels can be exploited in order to create seals between pre-formed structures. Solutions of sodium citrate (a chelator of $Ca^{2+}$) have been shown to effectively melt calcium-cross-linked alginate gels without damaging the chondrocytes (Masuda et al., *J. Ortho. Res.* 21:139-148 (2003); Ragan et al., *Arch. Biochem. Biophys.* 383:256-264 (2000), which are hereby incorporated by reference in their entirety). The surfaces of the pre-formed layers that are to be joined are coated with a dilute solution of sodium citrate (68 mM at pH 6.8) using an air brush (Badger 200NH, single-action air brush); this liberates cross-linkable acids at the surface of gel. Once coated, these surfaces are immediately placed in contact with one another immediately with light applied pressure and submerged in a solution of buffered $CaCl_2$. The excess calcium will allow the gel to fully re-form across the interface between the distinct layers. A variety of citrate concentrations will be tested in order to achieve the strongest possible link between the layers, while maintaining the surface structure.

An important step is the creation of fluidic connections between the embedded microfluidic scaffolds and external tubing. A solid support for the alginate gels can be created by sand-blasting holes in a standard microscope slide (Fisher), and gluing short segments of roughened Tygon tubing (SmallParts) into these holes. Rubber septa (Fisher) is glued to the underside of the glass slide to provide a re-sealable puncture surface. By casting the unstructured gel directly onto this pre-assembled support, fluidic connections are automatically incorporated into the alginate gel; roughening of the tubing ensures good mechanical adhesion of the gel to the glass slide. Sealing the structured layer to the unstructured layer then results in a closed fluidic circuit. This assembled cartridge is used in conjunction with another platform in which precisely positioned hypodermic needle tips pierce through the rubber septa, providing a re-sealable connection to the external pumping system (peristaltic pump).

In order to develop a quantitative understanding and control of mass transfer in 3D tissue scaffolds, numerical models of the convection-diffusion-reaction of metabolites and components of the extracellular matrix in cell-seeded alginate gels can be developed. Such a model builds on existing treatments of mass transfer in living tissues (Fournier, R., *Basic Transport Phenomena in Biomedical Engineering*; Taylor & Francis:Philadelphia (1998); Haselgrove et al., *Am. J. Physio.* 265:C497-C506 (1993); Obradovic et al., *Aiche Journal* 46:1860-1871 (2000); Malda et al., *Tissue Eng.* 10:987-994 (2004), which are hereby incorporated by reference in their entirety), and extends them to allow to account for the complex geometries of the microfluidic scaffolds. This model can be used to design microfluidic vascular networks that will allow for the imposition of the desired steady-state spatial distributions of solutes within the scaffolds. This can also enable one to account for transients associated with imposed changes in the culture conditions. To employ this model quantitatively for experimental design and evaluation, the diffusivities of the solutes of interest are measured within the scaffold as a function of the composition and history (e.g., time in culture) of the scaffold.

Described below is one approach to modeling convection-diffusion-reaction and to obtaining initial results on the distribution of oxygen in chondrocyte-seeded alginate scaffolds with embedded microchannels. Culture media with a known set of concentrations of reagents, will flow through the microchannels ($\{c_i^c\}$) and around the outside of the scaffold in the bioreactor ($\{c_i^b\}$). The mass transfer from the fluids into the scaffold will be modeled with mass transfer coefficients for each solute: $k_{b,i}(x, z, U_b, D_i^b)$ [m/s] for transfer from the reservoir, and $k_{c,i}(z, U_c, D_i^s)$ for transfer from the microchannels, where $U_b$ and $U_c$ [m/s] are flow speeds and $D_i^b$ and $D_i^s$ [$m^2$/s] are diffusivities in the reservoir and microchannels respectively. The values of $k_b$ and $k_c$ can be estimated from established correlations (Perry et al., *Perry's Chemical Engineer's Handbook*, 6th Ed., New York:McGraw-Hill, Inc. (1984), which is hereby incorporated by reference in its entirety), and these values can be measured directly for bioreactor design. The concentration of the $i^{th}$ species is governed by a reaction-diffusion equation with information about the convection in the reservoir and the channels expressed in the mass transfer coefficients, $k_{b,i}$ and $k_{c,i}$:

$$\frac{\partial c_i}{\partial t} = D_i^s \nabla^2 c_i + R_i(\{c_j\}, t), \text{ with} \tag{1a}$$

$$\nabla_n c_i(r_c) = -\frac{k_{c,i}}{D_i^s}[c_i(r_c) - c_i^c] \text{ and } \nabla_n c_i(r_b) = -\frac{k_{b,i}}{D_i^s}[c_i(r_b) - c_i^b]. \tag{1b}$$

In Equation (1a), $R^i$ [mole/$m^3$s] is the reaction rate of the $i^{th}$ species, which, in general, can depend on the concentration of other species, $c_j$, and time. Although reactions will mostly occur in the discrete volumes of the cells, a continuum approximation will be used such that $R_i = \rho_{cell} R_{i,cell}$, where $\rho_{cell}$ [cells/$m^3$] is the cell density, and $R_{i,cell}$ [moles/cell s] is the rate per cell. In Equations (1b) for the boundary conditions, $\nabla_n$ represents the normal gradient at the boundary of either the reservoir ($r_b$) or the channels ($r_c$). For a given set of culture conditions as defined by $\{c_i^b\}$, $\{c_i^c\}$, $k_{b,i}$, $k_{c,i}$, geometrical parameters, and rate laws, $R_i$, Equations (1) are solved simultaneously for coupled species using finite element analysis within FEMLab (unstructured meshes of triangles with the non-linear solving package).

As examples, below are approaches for treating the specific cases of oxygen consumption and GAG production:

Oxygen:

Metabolites such as oxygen are consumed by cells within the volume of the tissue by irreversible processes that are typically well described by Michaelis-Menten kinetics, such that $$R_{O2,cell} = -v_{max,O2} \frac{c_{O2}}{c_{O2} + K_{M,O2}}, \quad (2)$$

where $v_{max,O2}$ [mole/cell s] is the maximum rate of oxygen consumption per cell, and $K_{M,O2}$ is the Michaelis constant; both of these parameters are specific to the metabolite and to the type and status of the cells (Stryer, L., *Biochemistry*, 4th ed., New York:W.H. Freeman and Co. (1995); Obradovic et al., *Aiche Journal* 46:1860-1871 (2000), which are hereby incorporated by reference in their entirety). This assumption can be updated if evidence shows that the metabolism of oxygen varies significantly within the range of culture conditions (see Lee et al., *Biochemical Journal* 321:95-102 (1997), which is hereby incorporated by reference in its entirety). It is assumed that these kinetic parameters are constant with respect to the concentrations of all species, including oxygen. These calculations are run for 5% oxygen tension in the media in both the reservoir and the microchannels, and at cell seeding densities, $\rho_{cell}=10^7$ cell/mL and $\rho_{cell}=5\times10^7$ cells/mL. In the non-microfluidic scaffolds at high seeding densities, the tension was found to vary between $p_{O2}=4.1\%$ and 0.05% and nearly half (46%) of the tissue is anoxic ($p_{O2}<1\%$), whereas the delivery of oxygen via the microchannels was found to maintain the entire scaffold in a window of oxygen tensions between 1.6 and 4.7%.

Proteoglycans:

There is not currently a single accepted model for the dependence of the rate of ECM production on the culture environment. As a first step toward developing such as model, the monolithic biomaterial of the present invention can be used to perform simultaneous measurements of concentrations of oxygen tension and GAG production. These data can be compared to solutions of Equations (1) in order to test two models of the oxygen dependence of the rates of GAG synthesis: zeroth order in oxygen and first order in oxygen with the possibility of self limitations in both cases. The diffusion of newly synthesized GAG is neglected; this step is based on the assumption that these molecules are quickly incorporated into high molecular weight proteoglycans (Obradovic et al., *Aiche Journal* 46:1860-1871 (2000), which is hereby incorporated by reference in its entirety). In this case, Equation (1a) for the concentration of GAG becomes:

$$\frac{\partial c_{GAG}}{\partial t} = \rho_{cell} R_{GAG,cell}. \quad (3)$$

The rates of generation per cell can have the following forms for first order ($R^1_{GAG,cell}$) or zeroth order ($R^0_{GAG,cell}$) dependencies on oxygen:

$$R^1_{GAG,cell} = k_{GAG,0}\left(1 - \frac{c_{GAG}}{c_{GAG,1}}\right)c_{o2} \text{ or } R^0_{GAG,cell} = k_{GAG,0}\left(1 - \frac{c_{GAG}}{c_{GAG,1}}\right), \quad (4)$$

where $k_{GAG}$ is a rate constant, $c_{GAG,1}$ is the self-limiting concentration of GAG (Obradovic et al., *Aiche Journal* 46:1860-1871 (2000), which is hereby incorporated by reference in its entirety), and $c_{O2}$ is the concentration distribution of oxygen that is either measured or calculated with Equation (1). These models can be tested quantitatively with spatially resolved measurements of both oxygen tension and relative GAG concentrations. Furthermore, Equations (1) and (3) are used to design microfluidic scaffolds that maintain controlled inhomogenous conditions for GAG synthesis.

These models can be updated as more experimental information is acquired. In particular, if it is observed that rate of GAG synthesis displays spatial distributions that are neither uniform (zeroth order in oxygen) or directly proportional to oxygen concentrations (first order), the system can be extended to consider other metabolites such as glucose that maybe strongly coupled to oxygen and GAG distributions.

Shear Stress on Walls of Microchannels:

Previous work indicates that hydrodynamic shear stress generated by perfusion of fluid through scaffolds can influence the development of chondrocytes (Kim et al., *Journal of Biomechanics* 28:1055-1066 (1995); Pazzano et al., *Biotechnology Progress* 16:893-896 (2000), which are hereby incorporated by reference in their entirety). Shear stresses at the walls of the microfluidic channels can be calculated as follows: $f_s \cong 6\eta U_c/w$ [N/m²], where $\eta$ (kg/m s) is the viscosity of the medium. In histological analyses, qualitative assessment can be made of the effects of this stress on chondrocyte development.

Research Design and Methods:

The monolithic biomaterial of the present invention can be used to study the feasibility and usefulness of microfluidic structure within 3D tissue culture scaffolds and the use of controlled distributions of soluble factors for the growth of complex meniscal cartilage (for example). Such studies can include the following three phases (i) preparation of microfluidic scaffolds; (ii) characterization of mass transfer within alginate constructs with embedded chondrocytes; and (iii) application of microfluidic vascular scaffold for the measurement of the effects of distributions of oxygen on the metabolic activity of chondrocytes in alginate scaffolds. Each of these phases is described below.

Preparation of Microfluidic Scaffolds with Embedded Bovine Meniscal Chondrocytes Design and Microfabrication of Microfluidic Master Structure:

Photolithography can be used to generate microstructures that will act as forms for molding microchannels into alginate-chondrocyte gels. This process is shown schematically in FIGS. 7A-7E. In order to form networks of microchannels with multiple thickness of channels, a multi-step lithographic procedure is followed, as shown in FIG. 7A-7B, and as described previously (Stroock et al., *Science* 295:647-651 (2002); Ng et al., *Electrophoresis* 23:3461-3473 (2002), which are hereby incorporated by reference in their entirety). Photomask: The design of each level of the microfluidic structure can be drawn with a computer aided design program (e.g., LEdit) and transferred to a chromium-on-glass photomask using the Pattern Generator (one of which is available at the Cornell Center for Nanoscale Science). Photolithography: Photolithography can be performed with the SU-8 series of negative photoresists (MicroChem, Newton, Mass.). For each set of microfeatures with a distinct thickness (proceeding from thickest to thinnest layer), photoresist can be spin cast to the desired thickness, pre-baked, exposed, and developed. The surface of the microstructures and the silicon substrate can be treated with fluorinated silane (tridecafluoro-1, 1,2,2-tetrahydrooctyl-1-trichlorosilane—Gelest Inc, Morrisville, Pa.) in order to inhibit adhesion to the silicone (McDonald et al., *Anal. Chem.* 74:1537-1545 (2002), which is hereby incorporated by reference in its entirety). A replica of the features can be generated in silicone (Sylgard 184, Dow Corning, Midland, Mich.). Prior to assembly into a mold and injection of alginate-chondrocyte pre-gel, the silicone master is to be oxidized for 15 seconds in a low temperature induction plasma (100 W, 300 Torr $O_2$ atmosphere—PDC-001 from Harrick, Ossining, N.Y.); this process is performed to render the surface of the silicone structure hydrophilic, and thus improve filling of the pre-gel into the features.

Fabrication of Macroscopic Mold

Macroscopic forms can be fabricated in RTV silicone elastomer (Dow Corning, Midland, Mich.) by molding existing structures (Chang et al., *Plastic and Reconstructive Surgery* 112:793-799 (2003), which is hereby incorporated by reference in its entirety) or structures formed by computer aided design and machining (Hott et al., *The Laryngoscope* 114: 1290-1295 (2004), which is hereby incorporated by reference in its entirety). In order to integrate multiple layers of microfluidic structure, a single macroscopic form can be used to generate a mold in several pieces. The molding process for a meniscus-shaped scaffold is illustrated schematically in FIGS. 7A-7E; in this example, the macroscopic form of the meniscus is reproduced in three independent layers: FIG. 7D shows an assembled mold in which the ceiling is defined by a silicone macro-mold of the top portion of a meniscus, and the floor is defined by a silicone micro-mold of the microfluidic network. FIG. 7E shows a sealed scaffold in which three layers of alginate-chondrocyte gels, each of which was defined independently as in FIG. 7D, have been sealed. In order to create macro-molds in multiple pieces, the original form can be partially submerged in silicone pre-polymer, this silicone can be cured, and the next layer of pre-polymer can be added, cured, and so on.

Injection Molding in Combined Micro and Macro-Mold

A micro-mold that presents microfluidic structures and a macro-mold that presents the desired global structure can be assembled in a rigid casing (machined in aluminum), as shown schematically in FIG. 7D. This structure can be clamped closed and maintained at 37° C. The suspension of chondrocytes in alginate is then to be rapidly mixed with a saturated solution of sterilized $CaSO_4$ (0.2 mg/mL of alginate solution) in PBS and injected with a syringe into the composite mold. Gelled structures are to be removed from the mold after 10 minutes, and allowed for further cross-linking in a solution of $CaCl_2$ (80 mM) for 1 hour (Chang et al., *J. Biomed. Mat. Res.* 55:503-511 (2001) and Chang et al., *Plastic and Reconstructive Surgery* 112:793-799 (2003), which are hereby incorporated by reference in their entirety).

Sealing and Fluidic Connections

The methods employed to create a microfluidic structure in 4% acellular calcium alginate can be extended to work with cell-seeded gels, and with alginate gels of different concentrations (2% and 6%). Fluidic connections can be made by embedding short segments of roughened Tygon tubing into the alginate gel during the casting step. All of the methods in acellular gels are compatible with sterile procedures.

Another aspect of the present invention relates to a method of facilitating healing of a cutaneous wound of a mammalian subject. This method involves providing a monolithic biomaterial of the present invention. The monolithic biomaterial is contacted with a cutaneous wound (e.g., acute and/or chronic wounds) of the mammalian subject (e.g., humans). At least one healing agent is then introduced into the primary network of microfluidic channels under conditions effective to allow for convective transport of the healing agent through the microfludic channels and for diffusive transport of the healing agent into the substrate, thereby facilitating healing of the wound.

Suitable healing agents for use in this method can include, without limitation, growth factor, proteinase, a pharmacological agent, collagenase, gallium nitrate, oxygen, and/or combinations thereof.

In one embodiment, introducing the healing agent into the primary network of microfluidic channels involves controlling the flow of the healing agent through the microfluidic channels. In particular, this can include, without limitation, spatially and/or temporally controlling the healing agent concentration near or at the wound.

In another embodiment, the method can include applying a biocompatible material to the surface of the wound prior to contacting the monolithic biomaterial to the wound. Suitable biocompatible materials can include, without limitation, an aliginate, an acrylate-based hydrogel, collagen, and a collagen-glycosamino-glycan co-precipitate.

In another embodiment, the method can further include providing a fluid driving system for introducing the at least one healing agent into the primary network of microfluidic channels, thereby allowing for convective transport of the healing agent through the microfludic channels and for diffusive transport of the healing agent into the substrate.

A suitable fluid driving system can include a flow generator and a flow evacuator. A suitable flow generator includes, for example, a peristaltic pump. A suitable flow evacuator includes, for example, a vacuum-generating device.

Yet a further aspect of the present invention relates to a method of regulating cells. This method involves providing a monolithic biomaterial of the present invention. Fluids are allowed to flow through the microfluidic channels under conditions effective to regulate cells in or proximate to the monolithic biomaterial. This method can be used for tissue engineering, either in vitro or in vivo. In this method, the biomaterial can act as a template for cell growth. For example, the biomaterial can serve as a source of cells (e.g., viable cells embedded in the substrate of the biomaterial) and/or as a conduit for connecting and proliferating cellular tissue (e.g., vascular or nerve tissue) originating from a mammalian subject.

In one embodiment of this method of regulating cells, the biomaterial is provided in vitro. In another embodiment, the biomaterial is provided in vivo. Suitable ways of providing the biomaterial in vivo is by implanting the biomaterial into a mammalian subject or attaching the biomaterial to the surface of the mammalian subject.

Suitable cells that can be regulated by this method can include, without limitation, all prokaryotic and eukaryotic (e.g., mammalian and plant) cells. Examples of suitable mammalian cells that can be regulated by this method can include, without limitation, nerve cells, blood vessel cells, and cutaneous cells. More particularly, suitable cells that can be regulated by this method can include, without limitation, chondrocytes, osteoblasts, osteoclasts, osteocytes, fibroblasts, hepatocytes, skeletal myoblasts, cardiac myocytes, epithelial cells, endothelial cells, keratinocytes, neurons, Schwann cells, oligodendrocytes, astrocytes, pneumocytes, adipocytes, smooth muscle cells, T cells, B cells, marrow-derived stem cells, hematopeotic stem cells, osteoprogenitor cells, neural stem cells, and embryonic stem cells.

In one embodiment of this method of regulating cells, the fluids are allowed to flow through the microfluidic channels by introducing the fluids into the primary network of microfluidic channels under conditions effective to allow for convective transport of the fluids through the microfludic channels and for diffusive transport of the fluids into the substrate, thereby regulating cells in or proximate to the biomaterial.

Introducing the fluids into the primary network of microfluidic channels can involve controlling the flow of the fluids through the microfluidic channels. In particular, this can include, without limitation, spatially and/or temporally controlling the fluids concentration throughout the network.

In another embodiment, the method can further include providing a fluid driving system for introducing fluids into the primary network of microfluidic channels, thereby allowing for convective transport of the fluids through the microfludic channels and for diffusive transport of the fluids into the substrate. A suitable fluid driving system for use in this method of regulating cells is as described above.

The fluids used in this method can include solutes. Suitable solutes can include, for example, peptides (e.g., growth factors, enzymes, proteinases, collagenase,), soluble gases (e.g., oxygen and nitrogen), ions (e.g., sodium ions and chloride ions), pharmacological agents (e.g., gallium nitrate), genetic material (e.g., RNA, DNA, viral vectors, and viruses), neutral solutes (e.g., sugars), and combinations thereof.

EXAMPLES

The examples below are intended to exemplify certain aspects of the present invention but are by no means intended to limit the scope thereof.

Example 1

Fabrication of a Monolithic Biomaterial

A monolithic biomaterial was fabricated having a microfluidic system entirely within calcium alginate (4% [w/v]), a versatile hydrogel. As used herein this monolithic biomaterial is also referred to as a "microfluidic biomaterial" and abbreviated as "µFBM." Control of mass transfer within the ρFBM was demonstrated, and the µFBM was shown to be (i) appropriate for replication of the microstructure, (ii) formable into pressure-tight fluidic structures, and (iii) highly permeable to the diffusion of small and large solutes. The sealed microfluidic structure were formed to have channels that are 100 µm wide by 200 µm deep; sealed channels were formed with cross-sectional dimensions as small as 25 µm×25 µm.

Three modes of operation have been used to characterize the transfer of solute in µFBMs. In all cases, the device was submerged in a stirred reservoir (200 mL; $u_r$~1 cm/s) of aqueous buffer in which the solute of interest is dilute ($c_{s,r}$~0 mol/L); this reservoir acts as a sink for the solute in the gel. Pressure-driven flow ($u_c$~0.6 cm/s) of a distinct solution was used through the microchannels to either deliver ($c_{s,c}$=$c_0 \neq 0$ mol/L; channels act as sources) or extract ($c_{s,c}$=0 mol/L; channels act as sinks) the solute via the microfluidic network. These modes of operation are referred to as "assisted." Alternatively, no flow was imposed through the microchannels ($u_c$=0 cm/s) to assess the transfer of solute with the reservoir alone). This mode of operation is referred to as "unassisted."

These experiments illustrate that: (i) the µFBM in calcium alginate is sufficiently mechanically robust and impermeable to define distinct microfluidic paths (these devices have been tested up to positive pressures of 8 kPa and flow rates in the channels of $u_c$=1 cm/s); (ii) the material is permeable to the diffusion of both small and large molecules (a fit to a model of mass transfer in this geometry yields values for diffusivity in the gel that are close to those in free solution for both solutes); (iii) a steady concentration (and flux) of solute can be achieved in the µFBM by continuous delivery via the channels and extraction into the bulk; and (iv) the rate of exchange of solute with the gel is increased substantially by driving flows through the microchannels, as seen by the ~3.5 fold difference in the time required to reach 10% of the maximum intensity between assisted and unassisted extraction.

Materials for Preparing the Monolithic Biomaterial

SU-8 100 photoresin was obtained from Microchem and processed according to manufacturer specifications. Polydymethylsiloxane ("PDMS") (Dow-Corning, Sylgard 184) was obtained from Krayden, Inc. (Denver, Colo.) and processed according to manufacturer's specifications. (Tridecafluoro-1,1,2,2-tetrahydrooctyl)trichlorosilane was obtained from Gelest. Oxygen plasma treatments were performed in a plasma cleaner (model PDC-001, Harrick Scientific) on the highest setting. Track-etched polycarbonate membranes (Nucleopore 0.2 µm pore size, Whatman, www.whatman.com), Tygon tubing (O.D. 1/16"), and a Fisherbrand variable speed peristaltic pump were obtained from Fisher Scientific. Medical grade adhesive (MG 30 Instant Adhesive, Adhesive Systems Inc.) was obtained from McMaster-Carr. Alginate (LF10/60) was obtained from FMC Biopolymer as a powder and stored at −20° C. until use. Calcium chloride, N-(2-hydroxyethyl)-piperazine-N'-2-ethanesulfonic acid (HEPES), sodium chloride, sodium citrate, fluorescein salt, Rhodamine B isothiocyanate-Dextran (RITC-dextran, MW=70 kDa), poly(ethylenimine) (branched, M.W.=750 kDa), were obtained from Aldrich.

Photolithography

As illustrated in FIGS. 2A-2B, contact photolithography was used to fabricate master structures in SU-8 on 4-inch silicon wafers. These masters acted as molds for a secondary master in PDMS. This double molding was necessary, because alginate gels did not release easily from SU8-on-wafer structures. The surface of the SU8-on-wafer structure was passivated with the deposition of a fluorosilane in an evacuated desiccator as described previously (McDonald et al., *Analytical Chemistry* 74:1537-1545 (2002), which is hereby incorporated by reference in its entirety); this step inhibits adhesion of PDMS to the silicon.

Molding and Release of Elastomeric Mold

Molding and release of the elastomeric mold are illustrated in FIGS. 3A-3B. The secondary master in PDMS was created by pouring the pre-polymer onto the SU8 master and curing in the oven at 60° C. for 2 hours. This PDMS impression was oxidized for 60 seconds in an oxygen plasma immediately before each use in order to increase its wettability by the sodium alginate solution.

Molds Assembly

Mold assembly is illustrated in FIGS. 4A-4B. Two jigs were assembled: one for forming the micro-structured slab of alginate gel and one for forming the unstructured slab of gel. The ceiling of both jigs was formed by a track-etch polycarbonate membrane; this membrane allowed for diffusion of calcium into the gel during curing (cf. FIGS. 5A-5B). A closed mold for the micro-structured slab was formed by assembling one of the jigs with the PDMS stamp as the floor (FIG. 4A); the gap between the membrane and the PDMS defined the thickness of the molded gel. A closed mold for the bottom layer was formed by assembling the other jig with a standard microscope slide with pre-set tubing (FIG. 4B). The glass slide with pre-set tubing provided support to the assembled alginate structure and facilitated fluidic connections between the embedded microfluidic network and external tubing. The slide-tubing assembly was prepared by sand-blasting holes through the slide, and gluing segments of Tygon tubing into these holes. To improve adhesion to the alginate gel, the tubing was roughened with coarse sandpaper before being glued. The slide-tubing assemblies were cleaned in an oxygen plasma for 60", and dip-coated with poly(ethylenimine) from a 0.1% solution in water. The slides were rinsed in ethanol before use.

Hydrogel Injection and Curing

Hydrogel injection and curing are shown in FIGS. 5A-5B. An alginate solution (4% [w/v] or ~260 µM) was injected with a syringe into the molds, and a solution of calcium chloride (60 mM) in HEPES buffer (150 mM NaCl, 15 mM HEPES; adjusted to neutral pH with 0.1 M NaOH) was placed in the upper reservoir of the jig, above the track-etched membrane. The pre-gel solution was allowed to gel for 60 minutes. After removal from the mold it was immediately used for the next step.

Surface Dissolution and Sealing

Surface dissolution and sealing are shown in FIGS. 6A-6B. Alginate is reversibly cross-linked when calcium is chelated by acids along the backbone of the polymers. The application of a soluble chelator of calcium dissolves a calcium alginate gel. Exploiting this property, seals between pre-formed slabs of calcium alginate gel were formed by partially melting the surfaces of the hydrogel sheets with sodium citrate, a chelator of calcium ions. The surfaces were coated with ~2 mg of a solution of sodium citrate (170 mM) using an air brush (Badger 200NH, single-action air brush). Once coated, the surfaces were immediately placed in contact with one another and kept in a sealed Petri dish (to retain moisture) for 60 minutes to allow the uncross-linked chains to interpenetrate. Next, the channels were filled with a solution of HEPES-buffered $CaCl_2$ (60 mM) via the embedded Tygon tubing, and the bi-layer was allowed to continue to re-gel in a bath of HEPES-buffered $CaCl_2$ for 60 minutes. Finished devices could be stored in a HEPES buffered solution (10 mM $CaCl_2$) for as long as 30 days prior to use.

Example 2

Experimental Methods for Delivery and Extraction of Fluorescent Dyes from µFBM

Fluid Handling

For all experiments, the µFBM (of Example 1) was submerged in a bath of 200 mL of HEPES-buffered solution with 10 mM $CaCl_2$ in a Petri dish (15 cm in diameter). The dish sat on a magnetic stir-plate that drove a stir-bar at 200 r.p.m. in the bath. The fluid in the bath was changed before each assisted delivery. The assembly was covered by ~0.5 cm of liquid, and the average flow speed in the liquid was estimated to be, $u_r$~1 cm/s. This entire assembly sat on the stage of a fluorescence stereoscope.

Assisted Delivery

In order to deliver fluorescent dye to the µFBM, the inlet of the microfluidic network was connected to an elevated reservoir; the meniscus in the reservoir was maintained ~10 cm above the sample. A peristaltic pump was attached to the outlet. The flow rates through the system could be regulated between 85 to 150 µL/min ($u_c$=0.4-0.7 cm/s) with the controls of the pump. Solutions of fluorescein (20 µM) or RITC-dextran (10 µM) in HEPES-buffered solution were delivered from the elevated reservoir. Delivery was halted when steady state was achieved, as measured by the leveling off of the total measured intensity.

Assisted Extraction

In order to use the flow through the microfluidic network to evacuate dye from the gel, HEPES buffer containing no dye was placed in the elevated reservoir attached to the inlet. The flow of this non-fluorescent solution was again controlled with the peristaltic pump at the outlet. Evacuation was started from the steady state situation achieved at the end of the delivery.

Unassisted Extraction

In order to observe evacuation into the stirred bath alone, the flow through the microfluidic network was halted with the fluorescent solution still filling the channels. Again, the evacuation was started from the steady state achieved at the end of the delivery.

Fluorescence Microscopy and Image Analysis

The fluorescence images were taken on a Leica stereo microscope (MZ FLIII) using fluorescein and rhodamine filters, a mercury arc lamp, and a digital camera (Olympus DP 70). The images (1360×1024, jpeg format) were imported into Matlab, and the total intensity (summing all three color channels) was computed.

Example 3

Analysis of Mass Transfer in µFBM

Mass Transfer Conditions for All Experiments

The analysis and the operation of the µFBM (of Example 1) are greatly simplified at sufficiently high flow rates, where the bulk concentrations in the reservoir and the channels alone determine the concentration gradients driving the diffusion process. This condition is satisfied when the Biot numbers in both the reservoir and the channels are large, and the Peclêt number in the channels is large. The Biot number is defined as the ratio of the rate of mass transfer into the flow to the rate of diffusive mass transfer through the material, and is $$Bi = \frac{kH}{D_{s/gel}};$$

the Peclêt number is defined as the ratio of the rate of mass transfer with the flow to the rate of diffusion within the flow, and is $$Pe = \frac{u_c h}{D_{s/liq}}$$

(Welty et al., *Fundamentals of Momentum, Heat, and Mass Transfer* (2000), which is hereby incorporated by reference in its entirety). Here, $D_{s/gel}$ and $D_{s/liq}$ are the molecular diffusivities of the solute of interest in the gel and in the liquid; H=0.29 cm, and h=2×10$^{-2}$ cm. From the condition on the Peclêt number (Pe>>L/h), and L=1 cm, it has been found that $u_c$ must be greater than ~0.3 mm/s; from the condition on the Biot number (Bi>>1), $u_r$ must be much greater than ~1 cm/s. To calculate Bi, a standard form was used for the mass transfer coefficient for a flat plate in a stirred bath, $$k_r = 0.0443 \cdot \frac{D_{s/liq}}{d_{res}} \cdot Re^{0.785} \cdot Sc^{0.33} [cm/s],$$

where $d_{res}$ is the diameter of the reservoir, $\omega$ is the angular velocity of the reservoir fluid, $\rho$ and $\mu$ are the density and viscosity of water, Reynolds number, $$Re = \frac{d_{res}^2 \omega \rho}{\mu}$$

and the Schmidt number, $$Sc = \frac{\mu}{\rho D_{s/gel}}.$$

Assessment of Diffusivities of Dye Molecules in Calcium Alginate Gels from Unassisted Evacuation The temporal evolution of the fluorescence intensity in the µFBM during unassisted evacuation can be modeled approximately by considering diffusive transfer from a slab with infinite dimensions in x and y, and a thickness H in z. At high Bi, the predicted temporal evolution is a single exponential decay with a time constant, $$\tau_{slab} = \frac{4H^2}{\pi^2 D_{s/gel}}$$

[s] (Welty et al., *Fundamentals of Momentum, Heat, and Mass Transfer* (2000), which is hereby incorporated by reference in its entirety). Single exponential fits of the temporal evolution of unassisted evacuation (with H=0.29 cm) give Dfluor/gel ~5×10-6 cm2/s for fluorescein Ddex/gel=4×10-7 cm2/s for RITC-dextran. These numbers are comparable to values for the free diffusivities of these compounds in aqueous solution: Dfluor/H2O=6×10-6 cm2/s (Moore et al., *Analytical Chemistry* 65:3550-3560 (1993), which is hereby incorporated by reference in its entirety) and Ddex/H2O=4× 10-7 cm2/s (Lebrun et al., *Enzyme and Microbial Technology* 15:1057-1062 (1993), which is hereby incorporated by reference in its entirety). These predictions, although approximate, indicate that the calcium alginate gels used in this work were indeed highly diffusively permeable to both of these compounds.

Both delivery and extraction via the microchannels exhibit fast initial rate followed by a slower final rate, as seen by the slopes of the trace of assisted evacuation of fluorescein. These correspond to evacuation from the top part of the gel (faster because evacuated both via the channels and the reservoir), and the bottom part of the gel (evacuated via the microchannels only, hence slower). This behavior is in agreement with models of mass transfer in this geometry.

Example 4

Formation of Macroscopic, Three-Dimensional Scaffolds by Injection Molding of Alginate with Embedded Chondrocytes The appropriateness of alginate gels as scaffolds for 3D cultures of chondrocytes has been documented (Hauselmann et al., *Journal of Cell Science* 107:17-27 (1994), which is hereby incorporated by reference in its entirety). The chondrocytes are fully embedded in the gel by creating a suspension prior to gelation; gelation is induced by the infusion of calcium ions. It has been demonstrated that injection molding of the pre-gel suspension allows for the formation of scaffolds with well-defined 3-D shape of macroscopic dimension (>1 cm) (Chang et al., *J. Biomed. Mat. Res.* 55:503-511 (2001) and Chang et al., *Plastic and Reconstructive Surgery* 112: 793-799 (2003), which are hereby incorporated by reference in their entirety). As discussed below, this method involves the following steps: (i) isolation of chondrocytes; (ii) construction of molds; (iii) cell suspension in alginate; (iv) injection molding; and (v) implantation.

Isolation of Chondrocytes: Chondrocytes were isolated both from bovine articular cartilage from freshly slaughtered calf forelimbs, and from elastic cartilage in sheep ears (Chang et al., *Plastic and Reconstructive Surgery* 112:793-799 (2003), which is hereby incorporated by reference in its entirety). In both cases, the cartilage samples were minced and digested in solution of 3 mg/mL collagenase II at 37° C. for 12 to 18 hours, and the resulting suspension of cells was filtered, concentrated by centrifugation, and doubly washed with copious amounts of phosphate buffered saline.

Construction of Molds: Molds were prepared in room temperature vulcanizing (RTV) silicone rubber using commercially available silastic implants as a master structures. A two step molding process, with a partial cure of half the mold with embedded master, leads to a two part mold.

Cell Suspension in Alginate: Isolated cells were resuspended in a sterile solution of 2% sodium alginate in phosphate-buffered saline at pH 7.4. Cells were suspended at controlled concentrations from 10-50×10$^6$/mL. The brand of sodium alginate was Protanal LF 10/60 from FMC BioPolymer.

Injection Molding: Immediately before injection into molds, the cell suspension in alginate were mixed with sterilized CaSO$_4$ powder (0.2 mg/mL of alginate solution) in PBS solution; the calcium ions lead to physical cross-linking of the alginate. Note that CaSO$_4$ is sparingly soluble in buffer, so the rate of gelation is controlled by the slow dissolution of the CaSO$_4$, allowing for the pre-gel to flow for several seconds; this is an important aspect of the alginate material for molding processes. The chondrocyte/alginate/calcium solution was then injected in to the sealed, sterilized mold with a syringe. The gelled constructs were removed from molds after 10 minutes.

Implantation: Chondrocyte/alginate constructs were implanted subcutaneously for up to 30 weeks in the dorsal aspect of nude mice in the case of bovine chondrocytes (Chang et al., *J. Biomed. Mat. Res.* 55:503-511 (2001), which is hereby incorporated by reference in its entirety), or, autologously, in sheep in the case of sheep chondrocytes (Chang et al., *Plastic and Reconstructive Surgery* 112:793-799 (2003), which is hereby incorporated by reference in its entirety).

The harvested constructs maintained the 3-D shape that was imposed by the molding process. Biochemical (glycosaminoglycan ("GAG"), hydroxyproline, and DNA content) and mechanical (equilibrium modulus and hydraulic permeability) analyses were performed on harvested samples as a function of time and density of seeded cells. At the highest seeding density (50×10$^6$ cells/mL) and after 30 weeks, the GAG content reached 60% of the native value in sheep auricular cartilage, hydroxyproline content (a measure of collagen content) reached 80% of native, and DNA content reached 84% of native. The equilibrium modulus reached 74% of its native value and permeability dropped to within 10% of its native value. Histological samples prepared with Safranin O stain showed uniform distribution of proteoglycans, and cell morphology that is similar to that of native auricular cartilage. These results, and similar results with bovine chondrocytes, indicate that injection molding of chondrocytes in alginate gels is an effective means of generating scaffolds of well-defined macroscopic shape for engineering uniform cartilage samples.

Example 5

Biochemical Analysis of Long-Term Development of Cartilage in Molded and Sealed Scaffolds In order to assess the effects of the processes on the long-term viability and biosynthetic activity of chondrocytes, parallel cultures were performed in two types of alginate constructs: the controls were monolithic sheets of chondrocyte-seeded alginate of dimension 2 mm×8.5 mm×8.5 mm. The samples were bi-layers made from 1 mm-thick sheets of chondrocyte-seeded alginate; the total dimensions of the bi-layers were 2 mm×8.5 mm×8.5 mm. For all samples, the injection molding process of cell-seeded alginate was used (see Example 4). The alginate concentration was 2 wt. %, and the cell-seeding density was $5 \times 10^7/cm^3$. The sealing process used to form bi-layers involved 68 mM sodium citrate as a melting agent and osmotically balanced calcium chloride as a re-gelling agent. The citrate solution was applied to the surface of each calcium alginate sheet through a saturated cotton pad. The application method employed an airbrush to deliver the citrate, such that no physical contact was made with the gel and the volume applied tightly controlled. All samples were incubated in Dulbecco's Modified Eagle Medium (1×) at 37° C. and 5% $CO_2$ with media changed twice a week for zero to ten weeks. Biochemical analyses were performed.

Results were obtained from assays of the content (weight per wet weight of tissue) of DNA, glycosaminoglycans (GAG), and hydroxyproline (hypro, a measure of collagen). The data is based on 40 bi-layer samples and 32 monolithic samples. These data illustrate the following points: (i) the processing methods enable long-term survival of chondrocytes, as evidenced by steady state DNA levels that are similar to initial seeding density; (ii) chondrocytes remain biosynthetically active after molding and sealing, as evidenced by increases in ECM content with time; and (iii) steady state ECM content of bi-layer gels are similar to other studies (cf., Wilson et al., *Arch. Biochem. Biophys.* 408: 246-254 (2002), which is hereby incorporated by reference in its entirety).

Example 6

Characterization of Mass Transfer in Acellular Alginate Gels with Embedded Microfluidic Networks The mass transfer to and from acellular alginate gels with embedded microfluidic networks has been characterized. The gels were formed in 4% alginate as described herein. The microfluidic constructs were formed by sealing one microstructured sheet of alginate with a flat sheet of alginate (cf. FIGS. 7A-7E). The total dimension of each sheet was 2 mm×12 mm×12 mm; the global dimensions of the final structure was 4 mm×12 mm×12 mm.

An experiment was performed to characterize mass transfer with the bulk of the construct with and without an independent flow through the microfluidic channels. The fluid in the bath and run through the channel was HEPES buffer with 10 mM $CaCl_2$. The bath volume (200 mL) was stirred with a magnetic stir-bar. A peristaltic pump drove flow through the microchannels at flow rates between 70 and 140 µL/min. Experimental results were achieved for exchange of fluorescein (376 Da) and RITC-dextran (70 kDa).

These experiments illustrate (i) the feasibility of long-term operation of microfluidic structures in alginate (devices were run continuously out to 4 days and devices were used intermittently for up to two weeks), and (ii) the use of forced convection through embedded microchannels to increase rates of mass transfer to and from an alginate gel. For both high and low molecular weight species, the initial rate of evacuation (slope of plot) with forced convection ("assisted evacuation") through the microchannels was 4 times the rate with no internal flow ("unassisted").

Example 7

Adhesive Properties of Laminated Alginate Gels for Tissue Engineering of Layered Structures A significant challenge in tissue engineering is the creation of tissues with inhomogeneous or stratified morphology. Methods to fabricate composite gels from separately deposited alginate layers were studied and the effects of processing methods on the mechanics of adhesion were examined. Laminated alginate gels were created through a three step process which included: (i) treatment of the interfaces with citrate; (ii) annealing of the gels to allow for molecular rearrangement of the alginate chains; and (iii) exposure to a $CaCl_2$ to crosslink the alginate sheets. Process variables included volume and concentration of applied citrate, annealing time, incubation time in $CaCl_2$, and $CaCl_2$ concentration. Laminated sheets were tested in lap-shear geometry to characterize failure phenomena and mechanical properties. The site of failure within the gel depended on the integrity of the interface, with weaker gels delaminating and gels with mechanical properties similar to that of bulk gels failing randomly throughout the thickness. Citrate volume, citrate concentration, $CaCl_2$ incubation time, and $CaCl_2$ concentration altered the mechanical properties of the laminated alginate sheets, while annealing time had little effect on all measured parameters. As shown below, these experiments demonstrate the integration of separately fabricated alginate layers to create mechanically or chemically anisotropic or heterogeneous structures.

Hydrogels are commonly used in tissue engineering, in part due to their ability to form solid constructs with homogeneous distributions of cells (Lee et al., *Chem. Rev.* 101(7): 1869-1879 (2001), which is hereby incorporated by reference in its entirety). This is an advantage over other scaffold types such as foams or sponges, since it ensures uniformity in cell seeding. However, the ability to generate tissues with controlled, stratified morphology, like that of skin (Wang et al., *Tissue Eng.* 9(5):909-917 (2003), which is hereby incorporated by reference in its entirety) and cartilage (Wong et al., *J. Orthop. Res.* 14(3):424-432 (1996); Hunziker et al., *Osteoarthritis Cartilage* 10(7):564-572 (2002), which are hereby incorporated by reference in their entirety), remains a persistent challenge.

In order to utilize hydrogels to produce a heterogeneous distribution of cells within a construct, local or regional deposition of the seeded materials through methods such as layering is required. Recent studies have investigated methods to generate stratified articular cartilage constructs by depositing multiple layers of chondrocytes (Klein et al., *Osteoarthritis Cartilage* 11(8):595-602 (2003), which is hereby incorporated by reference in its entirety) or chondrocyte-seeded gels utilizing various materials including PEG (Kim et al., *Osteoarthritis Cartilage* 11(9):653-664 (2003), which is hereby incorporated by reference in its entirety) and agarose (Ng et al., *J. Orthop. Res.* 23(1):134-141 (2005), which is hereby incorporated by reference in its entirety). While these efforts show great promise, the properties of the interface between the layers limit the mechanical function of these constructs. This limitation is particularly important with hydrogels, which are mechanically weaker than other scaffold materials currently used for tissue engineering. To date, there has been little investigation into understanding the phenomena related to adhesion between successively deposited hydrogel layers.

Alginate, an anionic linear polysaccharide, has been used as a scaffold material for cartilage tissue engineering due to its support of the chondrocyte phenotype (Hauselmann et al., *J. Cell Sci.* 107(Pt 1):17-27 (1994), which is hereby incorporated by reference in its entirety), ability to be molded in desired shapes (Chang et al., *J. Biomed. Mater. Res.* 55(4): 503-511 (2001); Hott et al., *Laryngoscope* 114(7):1290-1295 (2004), which are hereby incorporated by reference in their entirety), support of chondrogenesis in large animal models (Chang et al., *Plast. Reconstr. Surg.* 112(3):793-799; Discussion 800-801 (2003), which is hereby incorporated by reference in its entirety), and biocompatibility in cell delivery in human trials (Vacanti et al., *N. Eng. J. Med.* 344(20):1511-1514 (2001), which is hereby incorporated by reference in its entirety). Cell types delivered using alginate include fibroblasts (Ponce et al., *Int. J. Pham.* 293(1-2):1-10 (2005), which is hereby incorporated by reference in its entirety), osteoblasts (Park et al., *J. Craniomaxillofac Surg.* 33(1):50-54 (2005); Li et al., *Biomaterials* 26(18):3919-3928 (2005), which are hereby incorporated by reference in their entirety), hepatocytes (Mai et al., *Transplant Proc.* 37(1):527-529 (2005); Lee et al., *J. Microbiol. Biotechnol.* 15(1):7-13 (2005), which are hereby incorporated by reference in their entirety), and pancreatic islets (Song et al., *Transplant Proc.* 37(1):253-255 (2005); Simpson et al., *Biomaterials* 26(22): 4633-4641 (2005), which are hereby incorporated by reference in their entirety). The mechanical properties of bulk alginate gels can be controlled with the type (LeRoux et al., *J. Biomed. Mater. Res.* 47(1):46-53 (1999); Drury et al., *Biomaterials* 25(16):3187-3199 (2004), which are hereby incorporated by reference in their entirety), molecular weight (Lee et al., *Chem. Rev.* 101(7):1869-1879 (2001); Kuo et al., *Biomaterials* 22(6):511-521 (2001); Kong et al., *Biomacromolecules* 5(5):1720-1727 (2004), which are hereby incorporated by reference in their entirety), and concentration (Lee et al., *Chem. Rev.* 101(7):1869-1879 (2001); LeRoux et al., *J. Biomed. Mater. Res.* 47(1):46-53 (1999); Kuo et al., *Biomaterials* 22(6):511-521 (2001); Kong et al., *Biomacromolecules* 5(5):1720-1727 (2004), which are hereby incorporated by reference in their entirety) of alginate in addition to the chemistry (Lee et al., *Chem. Rev.* 101(7):1869-1879 (2001); Kuo et al., *Biomaterials* 22(6):511-521 (2001); Genes et al., *Arch. Biochem. Biophys.* 422(2):161-167 (2004), which are hereby incorporated by reference in their entirety), delivery (Lee et al., *Chem. Rev.* 101(7):1869-1879 (2001); Genes et al., *Arch. Biochem. Biophys.* 422(2):161-167 (2004), which are hereby incorporated by reference in their entirety), and concentration (Lee et al., *Chem. Rev.* 101 (7):1869-1879 (2001); Kuo et al., *Biomaterials* 22(6):511-521 (2001); Genes et al., *Arch. Biochem. Biophys.* 422(2): 161-167 (2004), which are hereby incorporated by reference in their entirety) of cross-linker. Similarly, the removal of ionic crosslinks from alginate has also been studied in great detail (Lee et al., *Chem. Rev.* 101(7):1869-1879 (2001), which is hereby incorporated by reference in its entirety) such as the use of chelators including sodium citrate enabling the dissolution of alginate gels while maintaining viability of embedded cells (Klein et al., *Osteoarthritis Cartilage* 11(8): 595-602 (2003); Hauselmann et al., *J. Cell Sci.* 107(Pt 1):17-27 (1994); Chia et al., *Laryngoscope* 114(1):38-45 (2004), which are hereby incorporated by reference in their entirety).

While complete dissolution of alginate gels using chelators is employed commonly for cell retrieval, it is possible that controlled or focused application of such chelators could increase the mobility of the polymer in the gel state sufficiently to enhance adhesion of successively deposited gel layers. This possibility motivates the hypothesis that the interfacial mechanics of layered alginate gels can be enhanced through controlled application of crosslinking and chelating agents. Therefore the objectives of the below experiments were: (i) to develop methods to fabricate and evaluate the adhesion of separately deposited alginate layers; and (ii) to examine the effects of processing methods on the mechanics of adhesion.

Laminated Alginate Gel Formation

The protocol for casting alginate gels was based on that described previously for injection molding (Chang et al., *J. Biomed. Mater. Res.* 55(4):503-511 (2001), which is hereby incorporated by reference in its entirety). Briefly, two hydrogel sheets with a total volume of 4 ml were formed by mixing 20 mg/ml of low viscosity, high G content alginate [Protanal LF 10/60, FMC Biopolymer, Drammen, Norway] in Dulbecco's Phospate Buffered Saline [Gibco, Auckland, New Zealand] with 20 mg/ml $CaSO_4$ [Mallinckrodt Baker, Inc., Phillipsburg, N.J., USA] at a 2:1 volume ratio. The alginate and $CaSO_4$ solutions were mixed in two 10 ml syringes [Becton-Dickinson, Franklin Lakes, N.J., USA] connected via a three-way stopcock [Baxter, Deerfield, Ill., USA]. Once mixed, one hydrogel sheet was cast between two glass plates lined with parafilm [Pechiney, Menasha, Wis., USA] while the second sheet was cast between a parafilm-lined glass plate and a PDMS sheet to assist in the demolding process. In both cases, casting plates were separated by one millimeter spacers and allowed to set for 7 minutes, resulting in a one millimeter thick sheet of alginate.

One alginate sheet cast between glass plates was cut into 8.5 mm by 13 mm rectangles. The second sheet of alginate was partially de-molded with the removal of the glass plate. The resulting exposed sheet was then treated with sodium citrate with the application of an 85 mm by 70 mm paper wipe [kimwipe, Kimberly-Clark, Roswell, Ga., USA] to evenly distribute the solution. Concentrations ranging from 0 to 30 mg/ml and volumes ranging from 1 to 4 ml of sodium citrate were dripped onto the paper wipe with a 10 ml syringe while it was in contact with the alginate sheet. The paper wipe was carefully removed after an exposure time of two minutes. The treated alginate sheet was then lowered onto the cut alginate rectangles, producing a laminated structure of two separate alginate gels. The PDMS sheet of the mold was retained on the alginate gel to assist with lowering the alginate sheet onto the rectangles, after which point the PDMS sheet was removed. The layered sheets were placed into a mold consisting of 2 parafilm lined glass plates separated by 2 mm spacers and an 800 g weight was added on the top plate to ensure contact between the layers. The laminated gels were kept in contact for times ranging from 1 to 16 minutes, which is defined as the annealing time, allowing for molecular rearrangement and interdigitation at the gel-gel interface.

Following annealing, samples were transferred into a 200 ml bath of $CaCl_2$ [Sigma, St. Louis, Mo., USA] with concentrations ranging from 5 mg/ml to 40 mg/ml on a rotary mixer set at 40 RPM. Samples were maintained in the bath for times ranging from 30 seconds to 1 hour to reverse the effects of the calcium chelator. Upon removal from the $CaCl_2$ bath 8.5 mm×13 mm samples of the laminated alginate were cut out with a scalpel using the original alginate rectangles as a guide.

A total of five experiments were performed to test variables in the chemistry to produce the laminated alginate gels. Bulk 2 mm thick gels were created identically to the 1 mm thick gels, soaked for 8 min in a 20 mg/ml $CaCl_2$ bath and mechanically tested in the same manner to act as a reference to compare to the data generated from the laminated gels. Experiment one varied the concentration of sodium citrate applied to the gel from 0 to 30 mg/ml using 2 ml of sodium citrate with 8 minutes annealing time and 8 minutes in a 20 mg/ml $CaCl_2$ bath. Experiment two used a 15 mg/ml sodium citrate solution in varying volumes from 1 to 4 ml with 8 minutes annealing time and 8 minutes in a 20 mg/ml $CaCl_2$ bath. Experiment three varied annealing time from 1 to 16 minutes and used 2 ml of 15 mg/ml sodium citrate and 8 minutes in a 20 mg/ml $CaCl_2$ bath. $CaCl_2$ concentration was investigated in experiment four varying from 5 to 40 mg/ml with other parameters including 2 ml of 15 mg/ml sodium citrate, 8 minutes annealing time and 8 minutes in the $CaCl_2$ bath. Lastly, experiment five utilized 2 ml of 15 mg/ml sodium citrate, 8 minutes annealing time, 20 mg/ml $CaCl_2$ bath and expose to $CaCl_2$ was varied from 30 seconds to 1 hour.

Mechanical Testing

Immediately after creation, the laminate alginate gels were mechanically tested using a lap-shear test to measure the interfacial material properties (Matsumura et al., *J. Biomed. Mater. Res.* 60(2):309-315 (2002), which is hereby incorporated by reference in its entirety). Custom grips were fabricated consisting of strips of aluminum (8.5 mm wide) with a 1 mm offset bend. The resulting test geometry caused the direction of force to go through the interface of the gel ensuring that only shear and no moments were imposed at the gel-gel interface.

The layered samples were attached to the grips using cyanoacrylate glue. After both grips were attached to the samples, a small clamp was added around the grips in the sample region to add stability to the construct in order to move the sample to the test frame. The clamped grip-gel-grip assembly was loaded into an EnduraTEC ELF3200 mechanical test frame. Once the grips were secured in the test frame, the clamp was removed from assembly. Samples were pulled to failure at a displacement rate of 0.025 mm/sec, with load measured to within 1 g at a sampling frequency of 10 Hz.

Using sample geometry, displacements and loads were converted to strains and stresses. The resulting stress-strain curves enabled the calculation of the ultimate shear strength ("USS"), shear strain at failure or ultimate strain ("US"), shear modulus, and toughness. The ultimate shear strength is calculated as the maximum value of shear stress the sample was able withstand prior to failure and the strain at that point is denoted as the ultimate strain. The modulus was determined as the slope of the linear elastic region of the stress-strain curve. Toughness is the area under the stress-strain curve bounded by zero strain and the ultimate strain calculated with a Riemann sum technique (Peretti et al., *Tissue Eng.* 5(4):317-326 (1999); Peretti et al., *J. Biomed. Mater. Res. A.* 64(3):517-524 (2003), which are hereby incorporated by reference in their entirety). Throughout mechanical testing, the location of failure between the layered constructs was documented.

Normally distributed data was analyzed with a one way analysis of variance (p<0.05) with a Student-Newman-Keuls test for post hoc comparison. Data with a non-normal distribution was analyzed with a Kruskal-Wallis one way analysis of variance on ranks with Dunn's method utilized for post hoc comparison.

Experimental Results

The stress-strain behavior of bonded alginate gels was qualitatively similar to that of the bulk 2 mm thick gels. Bonded gels exhibited an extended linear region, after which the samples either yielded or failed directly. The ultimate strain achieved for both laminated gels and the bulk 2 mm gel was 0.13±0.04 and did not vary significantly due to variations in processing techniques.

The site of failure within the gel depended on the chemistry used to adhere the two alginate layers. The mechanically weaker layered gels delaminated at the adhesive interface, while bulk 2 mm gels and layered gels with comparable properties to the 2 mm bulk gels failed randomly throughout the thickness when subjected to lap shear.

Citrate Exposure

Ultimate shear strength increased with citrate concentration and volume up to 15 mg/ml and 2 ml, respectively, where a peak value of 2.68 kPa was reached and then dropped for both higher amounts of citrate and volume. Shear modulus increased with the addition of 7.5 mg/ml and 1 ml of citrate and did not change at higher concentrations and volumes. Toughness, similarly to USS, generally increased with increasing citrate concentration and volume, achieved a peak of 173.8 $J/m^3$ for 22.5 mg/ml and 156.3 $J/m^3$ for 2 ml then decreased with higher citrate concentrations and volumes. Statistically significant increases were noted with the application of citrate in USS [15-30 mg/ml, 2 and 3 ml], modulus [7.5-30 mg/ml, 1-4 ml], and toughness [15-22.5 mg/ml, 2 ml]. For all parameters there was a statistical difference (p<0.001) between properties generated with no citrate treatment to the laminated gels and the bulk 2 mm gels.

Annealing Time

Annealing time had little effect on all calculated parameters. No statistical difference was found in USS, modulus, and toughness with longer annealing times, nor the properties of the laminated gels compared to the 2 mm solid gels.

Calcium Chloride Exposure

Laminated gels exposed to 0 mg/ml $CaCl_2$ and those not exposed to $CaCl_2$ could not be tested due to extreme fragility that resulted in failure during the mounting process. Generally all mechanical properties increased with increasing $CaCl_2$ concentration. Exposure to 40 mg/ml $CaCl_2$ increased shear strength relative to 5 mg/ml (p<0.039) and produced laminated gels with similar properties to 2 mm bulk gels. A bath concentration of 40 mg/ml did produce a laminated construct which had a significantly higher modulus [47.6 kPa, p<0.012] than both laminated gels in a 5 mg/ml $CaCl_2$ bath and the bulk 2 mm gels (FIG. 6B). Toughness likewise increased with $CaCl_2$ concentration producing a maximum value of 255.9 $J/m^3$ at 40 mg/ml, however the result is not statistically significant.

Similarly, time of $CaCl_2$ exposure was found to have an effect on all mechanical properties evaluated. Ultimate shear strength increased with time of $CaCl_2$ exposure, although there was no significant difference found between time points or compared to 2 mm bulk gels. One hour in $CaCl_2$ bath produced laminated gels which had moduli that were significantly higher [478.3 kPa, p<0.0 12] than gels immersed in a bath for 30 seconds and 15 minutes. Toughness increased then decreased with a peak of 210.3 $J/m^3$ at 16 minutes with no significant difference over time in $CaCl_2$ or compared to bulk 2 mm gels.

Discussion

The results present in this example demonstrate the integration of separately fabricated alginate layers for the purpose of assembling multi-layered engineered tissues. Alginate sheets were held in apposition for short periods of time, mounted in grips, and pulled apart in a lap-shear geometry. Some integration of alginate sheets was observed in overlapping sheets after exposure to $CaCl_2$, producing mechanical properties similar to that of bulk 2 mm thick gels.

The adhesive properties of alginate layers were enhanced by the controlled application of sodium citrate, a chelating agent typically used to retrieve cells from alginate cultures (Klein et al., *Osteoarthritis Cartilage* 11(8):595-602 (2003); Hauselmann et al., *J. Cell Sci.* 107(Pt 1):17-27 (1994); Chia et al., *Laryngoscope* 114(1):38-45 (2004), which are hereby incorporated by reference in their entirety). It was hypothesized that controlled citrate exposure would remove calcium from the surfaces of alginate gels, so that subsequent exposure to $CaCl_2$ would augment bonding between sheets. Citrate exposure did enhance alginate adhesion as indicated most directly by the shear strength and toughness of the layered gels. Maximal enhancement was observed at 15 and 22.5 mg/ml citrate, but higher amounts of citrate weakened the gels. This phenomenon is possibly due to excessive reduction in cross-link density throughout the sample rather than localizing the chelation effects to the interface of the alginate sheets.

The annealing time had little effect on any of the mechanical parameters that were investigated, suggesting that the molecular mobility of the polymer chains at the interface was very high. Once the Ca++ ions were chelated at the interface, interdigitation between polymer chains from the two gel layers is not enhanced with longer annealing time. The laminated gels achieved properties similar to that of solid 2 mm gels within 1 minute of annealing time.

Calcium chloride treatment is an important step required to put Ca++ at the interface after initial gelation. Samples not treated with citrate but with $CaCl_2$ had minimal interfacial strength, but those without any $CaCl_2$ treatment resulted in no interfacial connection between the sheets. These data suggest that the key to forming laminated alginate gels is replacing intralaminar crosslinks with interlaminar crosslinks. The removal of intralaminar crosslinks at the gel surface is accomplished via citrate exposure, while interlaminar crosslinks are generated via $CaCl_2$ exposure. The increase in interfacial properties in cases of $CaCl_2$ treatment without citrate exposure suggests the presence of a small but finite density of potential crosslinking sites with sufficient mobility to cross the gel-gel interface. In contrast, the lack of interfacial adhesion in the absence of $CaCl_2$ exposure suggests that existing ionic crosslinks within the gel layers are not sufficiently mobile to form interlaminar crosslinks.

The maximum shear strength observed in the laminated gels is 10-70% that reported for intact alginate gels (LeRoux et al., *J. Biomed. Mater. Res.* 47(1):46-53 (1999); Drury et al., *Biomaterials* 25(16):3187-3199 (2004); Leung et al., *J. Dent.* 26(7):617-622 (1998), which are hereby incorporated by reference in their entirety), although the composition and testing methods for the reported gels differed from the current study. There is no comparable data for ultimate strain of alginate gels in shear. The ultimate strains reported here are much lower than those seen in tensile testing of alginate gels. Modulus and toughness however, are similar to those reported for alginate gels in tension and shear (LeRoux et al., *J. Biomed. Mater. Res.* 47(1):46-53 (1999); Drury et al., *Biomaterials* 25(16):3187-3199 (2004); Leung et al., *J. Dent.* 26(7):617-622 (1998), which are hereby incorporated by reference in their entirety). The laminated gels were able to be fabricated under various chemical conditions to produce values that were not statistically different from solid 2 mm thick gels tested in the system. This study validates the procedure to produce laminated alginate gels with properties similar to those reported for bulk gels made with other methods.

Based on data for mechanical properties as a function of the concentration and volume of citrate exposure, it is apparent that it is advantageous to minimize exposure of the bulk of the gel to chelators while ensuring exposure at the adhesive interface. In this study a paper wipe was used to uniformly distribute the sodium citrate solution, limiting citrate exposure to one surface of the gel. However, contact methods used to apply citrate may remove some of the uncrosslinked alginate. As a result, other techniques to reliably deliver a specified volume of a citrate solution to the surface of the alginate sheet, such as spraying, need to be developed.

The ability to deposit successive adhesive layers of alginate has many potential applications for tissue engineering. In addition to the prospect of creating heterogeneous cell populations by layer, this technique can also be applied to create mechanically or chemically anisotropic or heterogeneous structures that more effectively match native tissues. Further, this technique can be used with other fabrication and lithography techniques to embed topographic features in layers to create microfluidic systems to engineer vascular tissues.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A monolithic biomaterial comprising:
    a substrate which is diffusively permeable to aqueous solutes and capable of supporting living cells when seeded in the substrate and
    a primary network of convective flow, microfluidic channels embedded in the substrate, whereby aqueous solutes in the substrate will diffuse into said primary network of convective flow, microfluidic channels.

2. The monolithic biomaterial according to claim 1, wherein said substrate comprises a hydrogel.

3. The monolithic biomaterial according to claim 2, wherein said hydrogel is selected from the group consisting of alginate, an acrylate-based hydrogel, collagen, and a collagen-glycosamino-glycan co-precipitate.

4. The monolithic biomaterial according to claim 2, wherein said hydrogel is seeded with a plurality of viable cells.

5. The monolithic biomaterial according to claim 4, wherein said viable cells are of multiple cell types.

6. The monolithic biomaterial according to claim 4, wherein said viable cells are seeded on or proximate to a wall of at least one of the microfluidic channels.

7. The monolithic biomaterial according to claim 4, wherein said viable cells are homogeneously dispersed throughout the hydrogel.

8. The monolithic biomaterial according to claim 4, wherein said viable cells comprise chondrocytes.

9. The monolithic biomaterial according to claim 2, wherein said hydrogel further comprises a cross-linking compound.

10. The monolithic biomaterial according to claim 9, wherein said hydrogel comprises alginate and the alginate and the cross-linking compound are present in a ratio of about 1:100 to 100:1, respectively.

11. The monolithic biomaterial according to claim 1, wherein said substrate has an anatomic shape.

12. The monolithic biomaterial according to claim 1, wherein said primary network of microfluidic channels comprises a plurality of main microfluidic channels arranged substantially parallel to one another.

13. The monolithic biomaterial according to claim 12, wherein said primary network of microfluidic channels further comprises a plurality of subsidiary microfluidic channels arranged substantially perpendicular to said main microfluidic channels.

14. The monolithic biomaterial according to claim 1, wherein said primary network of microfluidic channels comprises a plurality of main microfluidic channels having subsidiary microfluidic channels branching from said main microfluidic channels.

15. The monolithic biomaterial according to claim 14, wherein said subsidiary microfluidic channels have cross-sectional dimensions that are smaller than those of the main microfluidic channels.

16. The monolithic biomaterial according to claim 1 further comprising at least one inlet portion suitable for delivering an incoming fluid into the primary network of microfluidic channels and at least one outlet portion suitable for removing an outgoing fluid from the primary network of microfluidic channels.

17. The monolithic biomaterial according to claim 1 further comprising a secondary network of microfluidic channels in the substrate, wherein said secondary network is independent from the primary network.

18. The monolithic biomaterial according to claim 17, wherein said primary network and said secondary network are separated by a diffusively permeable material.

19. The monolithic biomaterial according to claim 17 further comprising at least one inlet portion suitable for delivering an incoming fluid into the primary and secondary network of microfluidic channels and at least one outlet portion suitable for removing an outgoing fluid from the primary and secondary network of microfluidic channels.

20. The monolithic biomaterial according to claim 1, wherein said microfluidic channels have cross-sectional dimensions comprising between about $1\times10^{-1}$ μm to about $1\times10^{3}$ μm in width and between about $1\times10^{-1}$ μm to about $1\times10^{3}$ μm in height.

* * * * *

UNITED STATES PATENT AND TRADEMARK OFFICE
CERTIFICATE OF CORRECTION

PATENT NO. : 8,663,625 B2
APPLICATION NO. : 11/251707
DATED : March 4, 2014
INVENTOR(S) : Stroock et al.

Page 1 of 1

It is certified that error appears in the above-identified patent and that said Letters Patent is hereby corrected as shown below:

In the Claims:

Column 34, line 20, delete "$1\times10^{\sim}1$" and insert in its place --$1\times10^{-1}$--.

Signed and Sealed this
Eighth Day of July, 2014

Michelle K. Lee
*Deputy Director of the United States Patent and Trademark Office*